US012233109B2

(12) United States Patent
Lee et al.

(10) Patent No.: US 12,233,109 B2
(45) Date of Patent: *Feb. 25, 2025

(54) LONG-ACTING GLP-1r AGONIST AS A THERAPY OF NEUROLOGICAL AND NEURODEGENERATIVE CONDITIONS

(71) Applicant: The Johns Hopkins University, Baltimore, MD (US)

(72) Inventors: Seulki Lee, Baltimore, MD (US); Ted M. Dawson, Baltimore, MD (US); Han Seok Ko, Baltimore, MD (US); Valina L. Dawson, Baltimore, MD (US); Seung Pil Yun, Baltimore, MD (US); Magdalena Scully, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,428

(22) Filed: Sep. 20, 2021

(65) Prior Publication Data
US 2022/0111010 A1    Apr. 14, 2022

Related U.S. Application Data

(63) Continuation of application No. 16/065,445, filed as application No. PCT/US2016/068378 on Dec. 22, 2016, now Pat. No. 11,123,405.

(60) Provisional application No. 62/387,319, filed on Dec. 23, 2015.

(51) Int. Cl.
| | |
|---|---|
| *A61K 38/26* | (2006.01) |
| *A61K 9/00* | (2006.01) |
| *A61K 38/38* | (2006.01) |
| *A61K 47/60* | (2017.01) |
| *A61K 47/68* | (2017.01) |
| *A61P 25/16* | (2006.01) |
| *A61P 25/28* | (2006.01) |

(52) U.S. Cl.
CPC ............ *A61K 38/26* (2013.01); *A61K 9/0019* (2013.01); *A61K 38/38* (2013.01); *A61K 47/60* (2017.08); *A61K 47/68* (2017.08); *A61P 25/16* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 10,406,230 B2 * | 9/2019 | Lee | .................. C07K 14/57563 |
| 10,508,131 B2 | 12/2019 | Cox | |
| 2004/0242853 A1 | 12/2004 | Greig | |
| 2005/0009742 A1 | 1/2005 | Bertilsson | |
| 2005/0222036 A1 | 10/2005 | During | |
| 2006/0286066 A1 | 12/2006 | Basran | |
| 2007/0027306 A1 | 2/2007 | Rosen | |
| 2010/0323956 A1 | 12/2010 | Schellenberger | |
| 2012/0196795 A1 | 8/2012 | Xu | |
| 2013/0116172 A1 | 5/2013 | Dimarchi | |
| 2013/0116179 A1 | 5/2013 | Hess | |
| 2013/0137645 A1 | 5/2013 | Rosendahl | |
| 2013/0157934 A1 | 6/2013 | Dimarchi | |
| 2013/0217622 A1 | 8/2013 | Lee | |
| 2013/0281373 A1 | 10/2013 | Klein | |
| 2013/0303436 A1 | 11/2013 | Wilson | |
| 2014/0187490 A1 | 7/2014 | Richardson | |
| 2014/0220134 A1 | 8/2014 | Zierhut | |
| 2014/0301974 A1 | 10/2014 | Schellenberger | |
| 2015/0011462 A1 | 1/2015 | Reedtz-Runge | |
| 2015/0125431 A1 | 5/2015 | Just | |
| 2015/0164995 A1 | 6/2015 | Kadereit | |
| 2015/0164996 A1 | 6/2015 | Kadereit | |
| 2015/0164997 A1 | 6/2015 | Haack | |
| 2015/0166625 A1 | 6/2015 | Haack | |
| 2015/0166627 A1 | 6/2015 | Kadereit | |
| 2015/0306181 A1 | 10/2015 | Yi | |
| 2015/0376256 A1 | 12/2015 | Dimarchi | |
| 2016/0015788 A1 | 1/2016 | Holscher | |
| 2016/0101158 A1 | 4/2016 | Wilson | |
| 2016/0137698 A1 | 5/2016 | Skerra | |
| 2016/0287713 A1 | 10/2016 | Shen | |
| 2017/0189545 A1 | 7/2017 | Lee | |
| 2021/0353710 A1 * | 11/2021 | Duh | ........................ A61K 38/16 |

FOREIGN PATENT DOCUMENTS

| | | |
|---|---|---|
| AU | 2012202972 | 6/2012 |
| AU | 2013201640 | 4/2013 |
| AU | 2014277804 | 1/2015 |

(Continued)

OTHER PUBLICATIONS

Kopp, Katherine O. et al; "Glucagon-like peptide 1 (glp-1) receptor agonists and neuroinflammation: implications for neurodegenerative disease treatment." Pharm. Res. (2022) 186 (106550).*
Cherry, Johnathan D. et al; "Neuroinflammation and m2 microglia: the good, the bad, and the inflamed." J. Neuroinflam. (2014) 11(98).*
Finger, Carson E. et al; "Age related immune alterations and cerebrovascular inflammation." Mol. Psych. (2022) 27 p. 803-818.*
Brown, Becky; "12 most common causes of memory loss." Forbes, issue of Mar. 13, 2023.*
Costello, Paul; "Neurologist: the brain is complicated, largely unknown." Interview with Dr. Sharon Sha, May 11, 2020.*
The New Brunswick, Canada department of communicable disease control press release of 2021.*
Mathon, Bertrand et al; "Brain biopsy for neurological diseases of unknown etiology in critically ill patients: feasibility, safety, and diagnostic yield." CCM Journal (2022) 50(6) p. e516-e525.*

(Continued)

*Primary Examiner* — Fred H Reynolds
(74) *Attorney, Agent, or Firm* — PABST PATENT GROUP LLP

(57) ABSTRACT

The present invention relates to compositions and methods for treating neurodegenerative conditions using GLP-1r agonists. In certain embodiments, long-acting GLP-1r agonists have neuroprotective and disease modifying effects on the central nervous system.

32 Claims, 6 Drawing Sheets

Specification includes a Sequence Listing.

(56) References Cited

FOREIGN PATENT DOCUMENTS

| | | |
|---|---|---|
| CN | 101195612 | 6/2008 |
| CN | 103338790 | 10/2013 |
| CN | 106110325 | 11/2016 |
| EP | 1137666 | 10/2001 |
| EP | 1594529 | 11/2005 |
| EP | 1767545 | 3/2007 |
| EP | 1854455 | 11/2007 |
| EP | 2057189 | 5/2009 |
| EP | 2505941 | 10/2012 |
| EP | 2578599 | 4/2013 |
| EP | 2621538 | 8/2013 |
| EP | 2630965 | 8/2013 |
| KR | 1020020001719 | 1/2002 |
| KR | 1020070115602 | 6/2007 |
| KR | 1020110007362 | 1/2011 |
| WO | 200069911 | 11/2000 |
| WO | 0216430 | 2/2002 |
| WO | 2003011892 | 2/2003 |
| WO | 2004022004 | 3/2004 |
| WO | 2004023863 | 3/2004 |
| WO | 2005023862 | 3/2005 |
| WO | 2005077042 | 8/2005 |
| WO | 2006042848 | 4/2006 |
| WO | 2007075534 | 7/2007 |
| WO | 2008130066 | 10/2008 |
| WO | 2008148839 | 12/2008 |
| WO | 2010080578 | 7/2010 |
| WO | 2010121559 | 10/2010 |
| WO | 2011000095 | 1/2011 |
| WO | 2011003007 | 1/2011 |
| WO | 2011075393 | 6/2011 |
| WO | 2011143209 | 11/2011 |
| WO | 2012000118 | 1/2012 |
| WO | 2012012352 | 1/2012 |
| WO | 2012177444 | 12/2012 |
| WO | 2013002580 | 1/2013 |
| WO | 2013004983 | 1/2013 |
| WO | 2013009545 | 1/2013 |
| WO | 2013051938 | 4/2013 |
| WO | 2013148871 | 10/2013 |
| WO | 2013148966 | 10/2013 |
| WO | 2013192130 | 12/2013 |
| WO | 2014036323 | 3/2014 |
| WO | 2014041375 | 3/2014 |
| WO | 2014096145 | 6/2014 |
| WO | 2014110090 | 7/2014 |
| WO | 2014131815 | 9/2014 |
| WO | 2014152795 | 9/2014 |
| WO | 2014179983 | 11/2014 |
| WO | 2014202727 | 12/2014 |
| WO | 2015022400 | 2/2015 |
| WO | 2015086731 | 6/2015 |
| WO | 2015095406 | 6/2015 |
| WO | 2015132599 | 9/2015 |
| WO | 2015188132 | 12/2015 |
| WO | 2016011335 | 1/2016 |
| WO | 2016083499 | 6/2016 |
| WO | 2016097108 | 6/2016 |
| WO | 2016162127 | 10/2016 |
| WO | 2016198624 | 12/2016 |
| WO | 2016198628 | 12/2016 |
| WO | 2016205488 | 12/2016 |

OTHER PUBLICATIONS

Moore, Lisa; "Anencephaly." J. Diag. Med. Sonography (2010) 26(6) p. 286-289.*
Chen, Honglie et al; "Weight loss in parkinson's disease." Ann. Neurol. (2003) 53 p. 676-679.*
NIH news release of Dec. 13, 2013.*
Nguyen, Dung V. et al; "Inflammation in the pathogenesis of microvascular complications in diabetes." Front. Endocrinol. (2012)3 article 170.*
Witek, Natalie et al; "Neuroinflammation in parkinson's disease." Pract. Neurology (Sep. 2021) p. 44-48.*
DiSabato, Damon et al, "Neuroinflammation: the devil is in the details." J. Neurochem. (2016) 139(suppl 2) p. 136-153.*
Esin, R. G. et al, "Neuroinflammation and neuropathology." Neurosci. Behav. Physiol. (2022) 52(2) p. 196-201.*
Galea, Elena and Graeber, Manuel B.; "Neuroinflammation: the abused concept." ASC Neuro (2023) 15 p. 1-11.*
McClean, et al., "The Diabetes Drug Liraglutide Prevents Degenerative Processes in a Mouse Model of Alzheimer's Disease", The Journal of Neuroscience, 31(17):6587-6594 (2011).
Sengillo, et al., "Deficiency in Mural Vascular Cells Coincides with Blood-Brain Barrier Disruption in Alzheimer's Disease", Brian Pathology, 23(3):303-310 (2013).
Aisen, et al., "A randomized controlled trial of prednisone in Alzheimer's disease. Alzheimer's Disease Cooperative Study", Neurology, 54:588-93 (2000).
Aviles-Olmos, et al., "Exenatide and the treatment of patients with Parkinson's disease", J Clin Invest, 123(6):2730-6 (2013).
Ban, et al., "Cardioprotective and Vasodilatory Actions of Glucagon-Like Peptide 1 Receptor are Mediated Through Both Glucagon-Like Peptide 1 Receptor-Dependent and -Independent Pathways", Circulation, 2340-2350 (2008).
Berendsen, "A glimpse of the holy grail", Science 282:642-3 (1998).
Bomba, et al., "Exanatide promotes cognitive enhancement and poitive brain metabolic changes in PS1-KI mice but has no effets in 3xTg-AD animals", Cell Death & Disease, 4(5):e612 (2013).
Bradley, et al., Limits of cooperativity in a structurally modular protein: Response of the notch ankyrin domain to analogous alanine substitutions in each repeat, J Mol Biol, 324:373-86 (2002).
Byetta package insert, Amylin Pharmaceuticals, 2005.
Calsolaro, et al., "Novel GLP-1 (Glucagon-Like Peptide-1) Analogues and Insulin in the Treatment for Alzheimer's Disease and Other Neurodegenerative Diseases", CNS Drugs, 29:1023-1039 (2015).
Darsalia, et al., "Exendin-4 Reduces Ischemic Brain injury in Normal and Aged Type 2 Diabetic Mice and Promotes Microglial M2 Polarization", PLOS One, 9(8):e103114 (2014).
Davidson, "Advances in therapy for type 2 GLP-1 receptor agonists and DPP-4 inhibitors", Cleveland Clinic J Med., 76: Supp 5 (2009).
De Jong, et al., "No effect of one-year treatment with indomethacin on Alzheimer's disease progression: a randomized controlled trial", PLoS One, 23:e1475 (2008).
Definition of Analouge and Derivative, On-line medical Dictionary, accessed Mar. 5, 2000.
Definition of Dimer, thefreedictionary.com, 2 pages, accessed Dec. 8, 2014.
Definition of Trimer, thefreedictionary.com, 2 pages, accessed Dec. 8, 2014.
Dellavalle, et al., "GLP-1 improves neuropathology after murine cold lesion brain trauma", Annals of Clinical and Translational Neurology, 1(9):721-7323 (2014).
Diabetes, Diabetes sympotoins, The Mayo Clinic, https:// www. mayoclinic.org/diseases-conditions/diabetex/in-depth/diabetes-symptoms/art, accessed Dec. 9, 2014.
Farber, et al., "C1q, the recognition subcomponent of the classical pathway of complement, drives microglial activation", J Neurosci Res., 87(3):644-52 (2009).
Gold, et al., "Rosiglitazone monotherapy in mild-to-moderate Alzheimer's disease: results from a randomized, double-blind, placebo-controlled phase III study", Dement Geriatr Cogn Disord., 30:131-46 (2010).
Gong, et al., Site specific pegylation of exenatide analogues markedly improved their glucoregulatory activity., Brit. J. Pharmacol., 163:399-412 (2011).
Gong, et al., "Research paper: Site-specific PeGylation of exenatide analogues markedly improved their glucoregulatory activity", British J Pharma., 399-412 (2011).
Groeneveld, et al., "potentials of incretin-based therapies in dementia and stroke in type 2 diabetes mellitus", J. of Diabetes Investigation, 7(1):5-16 (2016).

(56) References Cited

OTHER PUBLICATIONS

Guadagno, et al., "Microglia-derived TNFα induces apoptosis in neural precursor cells via transcriptional activation of the Bcl-2 family member Puma", Cell Death and Disease, 4:e538 (2013).
Hansen, et al., "Long-Term Treatment with Liraglutide, a Glucagon-Like Peptide-1 (GLP-1) Receptor Agonist, Has No Effect on β-Amyloid Plaque Load in Two Transgenic APP/PS1 Mouse Models of Alzheimer's Disease", 11(7):e0158205 (2016).
Harkavyi, et al., "Glucagon-like peptide 1 receptor stimulation reverses key deficits in distinct rodent models of Parkinson's disease", Journal of Neuroinflammation, 5(19):1-9 (2008).
Harris and Chess, "Effect of pegylation on pharmaceuticals", Nat Rev Drug Discov, 2(3):214-21 (2003).
Hernandez, et al., "Topical Administration of GLP-1 Receptor Agonists Prevents Retinal Neurodegeneration in Experimental Diabetes", Diabetes, 65:172-187 (2015).
Hirsch, et al., "Neuroinflammation in Parkinson's disease: a target for neuroprotection", Lancet Neurol, 8:382-97 (2009).
Holscher, "Drugs developed for treatment of diabetes show protective effects in alzheimer's and parkinson's diseases", Acta Physiol. Sinica, 66(5):497-510 (2014).
Holscher, "Drugs developed for treatment of diabetes show protective effects in Alzheimer's and Parkinson's diseases", Acta Physiologica Sinica, 66(5):497-510 (2014).
Holscher, "Central effects of GLP-1: new opportunities for treatments of neurodegenerative diseases", J Endocrinol, 221(1): T31-41 (2014).
Hou, et al., "Liraglutide, a long-acting GLP-1 mimetic, and its metabolic attenuate inflammation after intracerebral hemorrhage", Journal of Cerebral Flow & Metabolism 32:2201-2210 (2012).
International Search Report for corresponding PCT application PCT/US2016/68378 mailed Apr. 21, 2017.
Iwai, et al., "Glucagon-like peptide-1 protects synaptic and learning functions from neuroinflammation in rodents", Journal of Neuroscience Research, (2014).
Kappe, et al., "GLP-1 secretion by microglial cells and decreased CNS expression in obesity", Journal of Neuro Inflammation, 9(276):1-10 (2012).
Kashikhara, et al. "Weight loss in parkinson's disease", J. Neural. , 253 (suppl.): pVIII-38-VII/41 (2006).
Kim, et al., "Mono-PEGylated dimeric exendin-4 as high receptor binding and long-acting conjugates for type 2 anti-diabetes therapeutics", Bioconjug Chem., 22(4):625-32 (2011).
Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).
Lang and Lozano, "Parkinson's disease. Second of two parts", N Engl J Med, 339(16):1130-43 (1998).
Le Tourneau, et al., "Dose escalation methods in phase I clinical cancer trials." J. Nat. Cancer Inst., 101:708-720 (2009).
Luk, et al., "Pathological α-synuclein transmission initiates Parkinson-like neurodegeneration in nontransgenic mice", Science, 338(6109):949-53 (2012).
Ma, et al., "Early intervention with glucagon-like peptide 1 analog liraglutide prevents tau hyperphosphorylation in diabetic db/db mice", Journal of Neurochemistry, 135(2):301-308 (2015).
Madison, et al., "Striatal blood-brain barrier permeability in parkinson's disease." J. Cerebral Blood Flow and Metab., 35: 747-750 (2015).
Martin, et al., "Exendin-4 Improves Glycemic Control, Ameliorates Brain and Pancreatic Pathologies, and Extends Survival in a Mouse Model of Huntington's Disease", Diabetes, American Diabetes Association, 58(2):318-328 (2009).
Meier, "GLP-1 receptor agonists for individualized treatment of type 2 diabetes mellitus", Nat Rev Endocrinol., 8(12):728-42 (2012).
Mondragon, et al; "Divergent effects of liraglutide, exendin-4, and stagliptin on beta cell mass and indicators of pancreatitis in a mouse model of hyperglycemia." PLOSOne, 9(8): e104873 (2014).
Montrose-Rafizadeh, et al., "Pancreatic Glucaon-Like Peptide-1 Receptor Couples to Multiple G Proteins and Activates Mitogen-Activated Protein Kinase Pathways in Chinese Hamster Ovary Cells", Endocrinology, 140(3):1132-1140 (1999).
Nagatsua and Sawadab, "L-dopa therapy for Parkinson's disease: past, present, and future", Parkinsonism Relat Disord, 15 Suppl (1):S3-8 (2009).
Ngo, et al., "Computational complexity", Protein Structure Protection and the Lecinthal Paradox, pp. 491-494 (1994).
Ninds Exploratory Trials in Parkinson Disease (NET-PD) FS-Zone Investigators, "Pioglitazone in early Parkinson's disease: a phase 2, multicentre, double-blind, randomised trial", Lancet Neurol., 14(8):795-803 (2015).
Pardridge, "The blood-brain barrier: bottleneck in brain drug development", NeuroRx 2(1): 3-14 (2005).
Patrone, et al., "Diabetes drugs and neurological disorders; new views and therapeutic possibilities", Diabetes & Endocrinology, 2(3):256-262 (2014).
Perry, et al., "Microglial priming in neurodegenerative disease", Nat Rev Neurol., 10:217-24 (2014).
Rudinger, "Peptide Hormones", JA Parsons, Ed pp. 1-7 (1976).
Saijo, et al., "A Nurr1/CoREST pathway in microglia and astrocytes protects dopaminergic neurons from inflammation-induced death", Cell, 137:47-59 (2009).
Sanchez-Guajardo, et al., "The relation between α-synuclein and microglia in Parkinson's disease: Recent developments", Neuroscience, 302:47-58 (2015).
Sandyk, "The relationship between diabetes mellitus and parkinson's disease", Intern. J. Neuroscience, 69:125-130 (1993).
Schernhammer, et al., "Diabetes and the Risk of Developing Parkinson's Disease in Denmark", Diabetes Care, 34:1102-1108 (2011).
Shannon, "Dpp-4 inhibition and neuroprotection: do mechanisms matter?" Diabetes, 62:1029-1031 (2013).
Sigma, "Design custom peptides", Sigma and Genosys, pp. 1-2 (2004).
Simuni and Brundin, "Is exenatide the next big thing in Parkinson's disease", J Parkinsons Dis., 4(3):345-7 (2014).
Taimr, et al., "Activated stellate cells express the Trail receptor-2/ death receptor-5 and undergo Trail-mediated apoptosis", Hepatology, 37(1):87-95 (2003).
Voet, "Abnormal hemoglobins", Biochemistry, (2):235-41 (1995).
Wahlqvist, et al., "Metformin-inclusive sulfonylurea therapy reduces the risk of Parkinson's disease occurring with Type 2 diabetes in a Taiwanese population cohort", Parkinsonism and Related Disorders, 18:753-758 (2012).
Xue, "Exendin-4 treatments of nonobase diabetic mice increases beta-cell proliferation and fractional insulin reactive area", J Diabetes Complic., 24:163-7 (2010).
Yu, et al., "Therapeutic bispecific antibodies cross the blood-brain barrier in nonhuman primates", Sci. Transl. Med., 6(261):261ra154 (2014).
Yun, et al., "Block of A1 astrocyte conversion by microglia is neuroprotective in models of Parkinson's disease", Nature Medicine, 24(7):931-938 (2018).
Yusta, et al., "GLP-1 receptor activation improves b cell function and survival following induction of endoplasmic reticulum stress", Cell Metabolism, 4:391-406 (2006).
International Search Report for PCT/US2016/068378 dated Apr. 21, 2017.
Kim, et al., "Exendin-4 protects dopaminergic neurons by inhibition of microglial activation and matrix metalloproteinase-3 expression in an animal model of Parkinson's disease", Journal of Endocrinology, 202:431-439 (2009).

\* cited by examiner

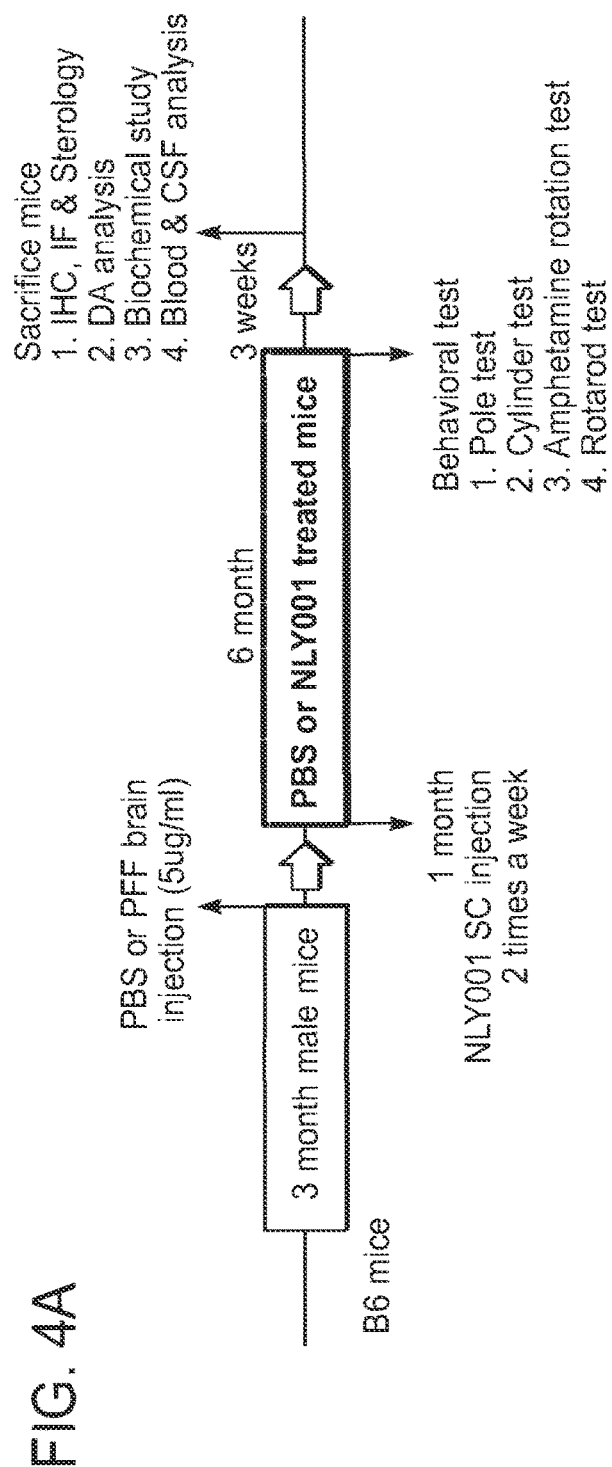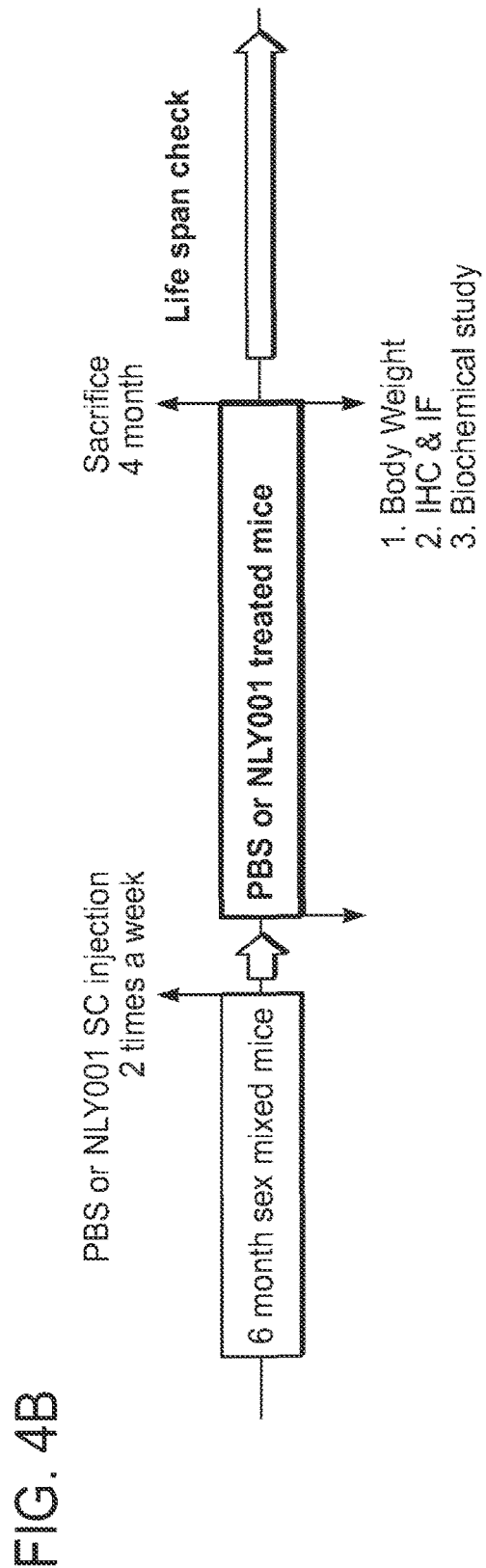
FIG. 4A
FIG. 4B

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

LONG-ACTING GLP-1r AGONIST AS A THERAPY OF NEUROLOGICAL AND NEURODEGENERATIVE CONDITIONS

RELATED APPLICATIONS

This application is a continuation of U.S. application Ser. No. 16/065,445, filed Jun. 22, 2018, which is a National Phase application under 35 U.S.C. 371 of PCT/US2016/068378, filed Dec. 22, 2016 entitled "LONG-ACTING GLP-1R AGONIST AS A THERAPY OF NEUROLOGICAL AND NEURODEGENERATIVE CONDITIONS", which claims the benefit of priority under 35 U.S.C. § 119(e) to U.S. Provisional Application No. 62/387,319, filed Dec. 23, 2015, which are incorporated herein by reference in their entirety.

REFERENCE TO SEQUENCE LISTING

The Sequence Listing submitted Sep. 20, 2021, as a text file named "JHU_C_13689_ST25.txt," created on Dec. 22, 2016, and having a size of 1,000 bytes is hereby incorporated by reference.

STATEMENT REGARDING FEDERALLY SPONSORED RESEARCH OR DEVELOPMENT

This invention was made with government support under NS082205 awarded by the National Institutes of Health (NIH). The government has certain rights in the invention.

BACKGROUND OF THE INVENTION

Neurodegenerative disease encompasses a range of conditions induced by the progressive loss of structure or function of neurons, including death of neurons. Diverse neurodegenerative diseases including Parkinson's disease (PD), Alzheimer's disease (AD), amyotrophic lateral sclerosis (ALS) and Huntington's disease (HD) occur because of neurodegenerative processes.

Parkinson's disease (PD) is a late onset, progressive neurodegenerative disorder that affects about one million Americans and 7 to 10 million people worldwide. Although dopamine replacement alleviates the symptomatic motor dysfunction, its effectiveness is reduced as the disease progresses, leading to unacceptable side effects such as severe motor fluctuations and dyskinesias. Moreover, this palliative therapeutic approach does not address the underlying mechanisms of the disease.

Alzheimer's disease (AD) is one of the most common neurodegenerative disease and accounts for more than 80% of dementia cases worldwide. It leads to the progressive loss of mental, behavioral, functional decline and ability to learn. Currently approved treatments, e.g. acetylcholinesterase inhibitors, only provide symptomatic improvement alone but do not modify the disease process. The number of new strategies including the amyloid and tau based therapeutics are in the clinical development, however, no drugs proved clear efficacy in humans prior to the invention described herein.

With people living longer, more people are developing these common, debilitating neurological disorders. Prior to the invention described herein, a proven neuroprotective therapy that can treat the disease or halt the progress of this disease in humans had not been identified. Therefore, there is a substantial unmet need for therapeutic strategies that treat this unrelenting progressive chronic disorder.

SUMMARY OF THE INVENTION

The present invention is based, at least in part, upon the development of long-acting GLP-1r (glucagon like peptide 1 receptor) agonists with neuroprotective and disease modifying effects on the central nervous system. A subcutaneously administered, long-acting exenatide was developed that, despite having a large molecular weight, has high bioactivity in the brain and significant neuroprotective and disease-modifying effects in mouse models of central nervous system disorders, e.g., neurodegenerative diseases. Engineered peptide drugs fused with large molecular weight half-life extension carriers, such as immunoglobulin Fc, albumin, or PEG, do not readily cross the blood-brain barrier (BBB) (Pardridge, W. M. 2005 NeuroRx 2(1): 3-14) unless the molecule is re-engineered to target BBB receptors such as the transferrin receptor (Yu Y. J. et al. 2014. Sci. Transl. Med. 6(261):261ra154). Described herein is a PEGylated exenatide (NLY001) with significantly improved half-life and mean residence time in non-human primates compared to BYETTA® exenatide (exendin-4 which has a 2 hour half-life) and liraglutide (which has a 13 hour half-life). PEGylated exenatide maintains its biological activity by a site specifically attached polyethylene glycol (PEG) molecule to exenatide (WO2013002580, incorporated herein by reference). Due to its greater half-life and potency, this compound is suitable for a once-weekly, bi-monthly or once-monthly clinical dosing frequency. This dosing frequency is an improvement over the current twice daily treatment (exenatide, BYETTA®) or once-daily treatment (liraglutide, VICTOZA®). However, like peptide drugs fused with large molecular weight carriers, this PEGylated exenatide was not expected to show efficacy in neurodegenerative diseases such as Parkinson's Disease (PD) or Alzheimer's Disease (AD) after systemic injection. As described herein, one unexpected discovery was subcutaneous administration of a long-acting GLP-1r agonist, PEGylated exenatide, demonstrates clear anti-Parkinson's Disease and anti-Alzheimer's diseases effects in clinically-relevant, transgenic PD and AD animal models through efficiently targeting activated microglia and reactive astrocytes in the brain. Described herein is the utilization of a long-acting GLP-1r agonist for the treatment of PD and AD as well as other neurodegenerative conditions, such as Huntington's disease and amyotrophic lateral sclerosis (ALS), the diseases that microglia activation centered pathogenesis.

Compositions and methods for selectively blocking or reversing microglia activation and reactive astrocytes, which are key cells involved in the establishment and/or progression of neurodegenerative diseases, to halt triggering of a cascade of neurotoxic pathways have been identified. The method includes administering a long-acting GLP-1r agonist to the subject.

In one embodiment, the method for treating or preventing neurodegenerative disease in a mammalian subject includes administering a long-acting GLP-1r agonist with the ability to penetrate BBB and activate GLP-1r in the PD brain in a continuous fashion without "off time" and without "off-target" toxicity. For example, a long-acting GLP-1r agonist, NLY001, efficiently accumulates in the brain of PD and AD models and, importantly, demonstrates slow GLP-1r internalization compared to that of short-acting GLP-1r agonists. Constitutive GLP-1r activation in the brain contributes to maximize synergistic anti-inflammatory and neuroprotection properties of GLP-1r agonist.

In one embodiment, the method of protecting neuronal cells acts by blocking gliosis (activation of microglia and astrocytes) and the release of toxic molecules from activated microglia and reactive astrocytes through targeting upregulated GLP-1r in activated microglia.

Accordingly, provided herein are methods of treating a neurodegenerative disease or disorder comprising administering to a subject suffering from or at risk of suffering from a neurodegenerative disease or disorder a pharmaceutically effective amount of a composition comprising a long-acting GLP-1r agonist to alleviate one or more symptoms of the neurodegenerative disease or disorder. Suitable long-acting GLP-1r agonist include a PEGylated GLP-1r analog, a Fc fusion GLP-1 analog, an albumin fusion GLP-1 analog, or a derivative thereof. In an exemplary aspect, the long-acting GLP-1r agonist comprises a PEGylated exenatide analog. In some cases, the neurodegenerative disease or disorder is selected from the group consisting of Parkinson's disease, Alzheimer's disease, Huntington's disease, amyotrophic lateral sclerosis, spinocerebellar ataxia type 1 (SCA1), and a prion disorder. Optionally, the neurodegenerative disorder is Parkinson's disease and Alzheimer's disease. In an exemplary embodiment, the methods further comprise identifying a patient suffering from or at risk of developing a neurodegenerative disease or disorder, e.g., Parkinson's disease or Alzheimer's disease.

Preferably, the long-acting GLP-1r agonist blocks activation of resident innate immune cells. For example, the innate immune cells comprise microglia and/or astrocytes. In some cases, abnormally aggregated proteins are inhibited from activating immune cells through upregulation of GLP-1r. For example, the abnormally aggregated proteins comprise α-synuclein, β-amyloid or tau. The amount of the long-acting GLP-1r agonist is effective to inhibit the secretion of inflammatory and/or neurotoxic mediators secreted from the activated innate immune cells.

In some cases, the GLP-1r agonist is administered in an amount effective to reduce inflammatory or neurotoxic mediators selected from the group consisting of TNF-α, IL-1α, IL-1β, IFN-γ, IL-6, and C1q as compared to an appropriate control. In one aspect, the GLP-1r agonist is administered in an amount effective to reduce the cell population of activated microglia and reactive astrocytes.

In one embodiment, the levels of TNF-α, IL-1α, IL-1β, IL-6 or C1q and/or activated microglia and reactive astrocytes in the brain are reduced, maintained or restored to, normal levels in the subject, as compared to an appropriate control.

In one embodiment, the levels of abnormal deposits of the brain protein such as alpha-synuclein (α-syn) (Lewy body) and amyloid plaques and tau are reduced, maintained at, or resorted to, normal levels in the subject, as compared to an appropriate control.

In one embodiment, the treatment alleviate or restores the motor deficit, improves memory functions and/or increases lifespan in the subject, as compared to an appropriate control.

Suitable modes of administration include oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, and subcutaneous administration. An exemplary mode of administration includes subcutaneous administration.

In some cases, the composition is administered in a form selected from the group comprising pills, capsules, tablets, granules, powders, salts, crystals, liquids, serums, syrups, suspensions, gels, creams, pastes, films, patches, and vapors.

In one aspect, the compositions described herein, e.g., PEGylated exenatide, are administered about 1-4 times a month. For example, the compositions are administered approximately once a week or twice a week. Alternatively, the compositions are administered approximately every two weeks. In other cases, the compositions are administered once a month. In other cases, the compositions are administered once every two months. In other aspects, the compositions are administered about 1-3 times every 6 months. Alternatively, the compositions of the invention are administered about 1-12 times a year, e.g., once a month, once every 2 months, once every 3 months, once every 4 months, once every 5 months, once every 6 months, once every 7 months, once every 8 months, once every 9 months, once every 10 months, once every 11 months, or once every 12 months.

Preferably, the compositions described herein, e.g., PEGylated exenatide, has an increased half-life in vivo, e.g., at least 2 hours to 200 hours. For example, the PEGylated exenatide has a half-life in vivo of 2 hours, 6 hours, 12 hours, 20 hours, 24 hours, 36 hours, 48 hours, 60 hours, 72 hours, 88 hours, 100 hours, 112 hours, 124 hours, 150 hours, 175 hours, or 200 hours. In an exemplary embodiment, the compositions of the invention comprise a half-life in vivo of 88 hours in non-human primates.

The compositions described herein are administered at a dose of 0.001 mg/kg to 100 mg/kg, e.g., 0.001 mg/kg, 0.01 mg/kg, 0.1 mg/kg, 0.5 mg/kg, 1.0 mg/kg, 2.0 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg. For example, the compositions are administered at a dose of between 0.2 mg/kg to 20 mg/kg in rodent models. In humans, the compositions can be administered at a dose between 0.001 mg/kg to 10 mg/kg.

In one aspect, the compositions described herein are administered to a subject for between 1 to 20 years, e.g., 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, or 20 years. Optionally, the compositions described herein are administered for 10 years. In one aspect, the effects of treatment last for at least 1 year.

Preferably, the compositions described herein protect against alpha-synuclein associated loss of dopaminergic neurons. In one aspect, the compositions described herein protect against amyloid-beta and/or tau toxicity in Alzheimer's disease neurons. For example, the compositions described herein protect against amyloid plaques and tau-associated loss of neurons. In one aspect, the compositions described herein improve motor and cognitive as well as memory skills in a subject relative to a control. In another aspect, the compositions described herein protect synapses and/or synaptic functions, enhance neurogenesis, reduce apoptosis, protect neurons from oxidative stress, reduce plaque formation, and prevent chronic inflammatory response in a subject relative to a control.

Also provided herein are compositions comprising long-acting glucagon like peptide 1 receptor (GLP-1r) agonists and one or more polyethylene glycol (PEG) moieties or derivatives thereof. In some cases, the long-acting GLP-1r agonist comprises a PEGylated GLP-1 analog or derivative thereof. In some cases, the long-acting GLP-1r agonist comprises an Fc fusion GLP-1 analog or albumin fusion GLP-1 analog or a derivative thereof. In some cases, the GLP-1r agonist is an Exendin-4 analogue and/or derivatives thereof. In some cases, the Exendin-4 analogue is a peptide. For example, the peptide comprises the sequence: HGEGTFTSDLSKQMEEEAVRLFIEW-LKNGGPSSGAPPPS (SEQ ID NO: 1).

In one aspect, the PEG moiety or derivative is selected from the group consisting of linear PEG, branched PEG, Star PEG, Comb PEG, dendrimeric PEG, PEG succinimidylpropionate, PEG N-hydroxysuccinimide, PEG propionaldehyde, PEG maleimide, linear methoxypoly(ethylene glycol) (mPEG), branched mPEG, Star mPEG, Comb mPEG, dendrimeric mPEG, mPEG succinimidylpropionate, mPEG N-hydroxysuccinimide, mPEG propionaldehyde, and mPEG maleimide. In some cases, the branched PEG moiety or derivative comprises monomeric, dimeric and/or trimeric PEG moieties, or derivatives thereof. In some cases, the PEG moiety or derivative is trimeric methoxypolyethylene glycol maleimide.

In another aspect, the PEG moiety comprises a PEG moiety of at least 1,000 daltons. In some cases, the PEG moiety comprises a PEG moiety within the range of 1,000-1,000,000 daltons. In other examples, the PEG moiety comprises a PEG moiety within the range of 10,000-500,000 daltons. In other cases, the PEG moiety comprises a PEG moiety within the range of 20,000-250,000 daltons. In other aspects, the PEG moiety comprises a PEG moiety within the range of 30,000-100,000 daltons. Alternatively, the PEG moiety comprises a PEG moiety within the range of 40,000-80,000 daltons. In an exemplary embodiment, the PEGylated exenatide described herein is NLY001, an exenatide PEGylated with a PEG moiety of 50,000 daltons.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

By "agent" is meant any small compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

By "binding to" a molecule is meant having a physicochemical affinity for that molecule.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence or amount of the analyte to be detected.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., prostate cancer, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

By a "long-acting GLP-1r agonist" is meant a GLP-1r agonist which is effective for at least one hour, at least six hours, at least twelve hours, at least one day, at least two days, at least one week, at least two weeks, at least one month, or at least two months.

By "marker" is meant any protein or polynucleotide having an alteration in expression level or activity that is associated with a disease or disorder.

By "modulate" is meant alter (increase or decrease). Such alterations are detected by standard art known methods such as those described herein.

By "neurodegenerative disease or disorder" is meant a general term for the progressive loss of structure or function of neurons, including death of neurons. Many neurodegenerative diseases including amyotrophic lateral sclerosis, Parkinson's, Alzheimer's, and Huntington's occur as a result of neurodegenerative processes. Such diseases are incurable, resulting in progressive degeneration and/or death of neuron cells.

The term, "normal amount" refers to a normal amount of a complex in an individual known not to be diagnosed with a disease or disorder. The amount of the molecule can be measured in a test sample and compared to the "normal control level," utilizing techniques such as reference limits, discrimination limits, or risk defining thresholds to define cutoff points and abnormal values (e.g., for prostate cancer). The "normal control level" means the level of one or more proteins (or nucleic acids) or combined protein indices (or combined nucleic acid indices) typically found in a subject known not to be suffering from prostate cancer. Such normal control levels and cutoff points may vary based on whether a molecule is used alone or in a formula combining other proteins into an index. Alternatively, the normal control level can be a database of protein patterns from previously tested subjects who did not convert to a disease or disorder over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

A "purified" or "biologically pure" nucleic acid or protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

By "reference" is meant a standard or control condition.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

As used herein, "obtaining" as in "obtaining an agent" includes synthesizing, purchasing, or otherwise acquiring the agent.

By "subject" is meant a mammal, including, but not limited to, a human or non-human mammal, such as a bovine, equine, canine, ovine, or feline. The subject is preferably a mammal in need of treatment, e.g., a subject that has been diagnosed with a disease or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The term "sample" as used herein refers to a biological sample obtained for the purpose of evaluation in vitro. With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "specifically binds" is meant a compound or antibody that recognizes and binds a polypeptide of the invention, but which does not substantially recognize and bind other molecules in a sample, for example, a biological sample, which naturally includes a polypeptide of the invention.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with heart disease, neurodegenerative disorders, and the like is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The terms "treat," "treating," "treatment," and the like as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

The term "PEGylation" refers to a process of both covalent and non-covalent attachment or amalgamation of polyethylene glycol (PEG) polymer chains to molecules and macrostructures, such as a drug, therapeutic protein or vesicle.

The terms "prevent", "preventing", "prevention", "prophylactic treatment" and the like refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

A "therapeutically effective amount" is an amount sufficient to effect beneficial or desired results, including clinical results. An effective amount can be administered in one or more administrations.

Any compositions or methods provided herein can be combined with one or more of any of the other compositions and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1 shows PK profiles of subcutaneously administered exenatide and NLY001 in cynomolgus monkeys (n=2). t½: half-life, MRT: mean residence time. The half-life of exenatide and Olaedin are 2.7±0.9 h and 88.0±10.9 h, respectively. The mean residence time of exenatide and Olaedin are 2.5±0.3 h and 114.0±17.5 h, respectively.

(FIG. 2C) Alzheimer's disease (n=6). *P<0.05, ***P<0.001.

FIG. 4A and FIG. 4B are diagrams showing a timeline that depicts the experimental strategy in complementary PD mouse models, (FIG. 4A) α-synuclein PFFs-induced PD models and (FIG. 4B) A53T α-synuclein transgenic PD models.

FIG. 5 shows immunostaining with antibody selective for α-synuclein LB (brown, arrow) in the brain tissues.

DETAILED DESCRIPTION OF THE INVENTION

Figure 1:
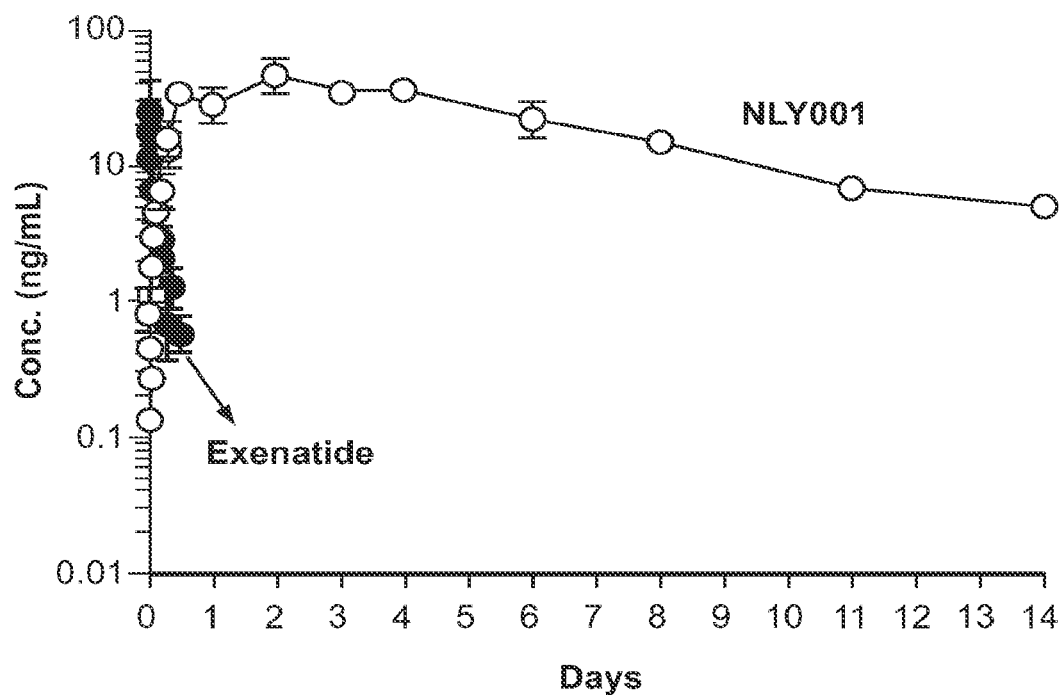
FIG. 1 depicts pharmacokinetic (PK) profiles of NLY001, a PEGylated exenatide.

Neurodegenerative disease encompasses a range of conditions induced by the progressive loss of structure or function of neurons, including death of neurons. Diverse neurodegenerative diseases including Parkinson's disease (PD), Alzheimer's disease (AD), amyotrophic lateral sclerosis (ALS) and Huntington's disease (HD) occur because of neurodegenerative processes.

Parkinson's disease (PD) is a late onset, progressive neurodegenerative disorder that affects about one million Americans and 7 to 10 million people worldwide. Although dopamine replacement alleviates the symptomatic motor dysfunction, its effectiveness is reduced as the disease progresses, leading to unacceptable side effects such as severe motor fluctuations and dyskinesias. Moreover, this palliative therapeutic approach does not address the underlying mechanisms of the disease (Nagatsua, T. and M. Sawadab, Parkinsonism Relat Disord, 2009. 15 Suppl 1: p. S3-8).

Alzheimer's disease (AD) is one of the most common neurodegenerative disease and accounts for more than 80% of dementia cases worldwide. It leads to the progressive loss of mental, behavioral, functional decline and ability to learn (Anand R et al., Neuropharmacology, 2014. 76 Pt A:27-50). Currently approved treatments, e.g. acetylcholinesterase inhibitors, only provide symptomatic improvement alone but do not modify the disease process. The number of new strategies including the amyloid and tau based therapeutics are in the clinical development, however, no drugs prove clear efficacy in humans yet.

With people living longer, more people are developing these common, debilitating neurological disorders. Prior to the invention described herein, a proven neuroprotective therapy that can treat the disease or halt the progress of this disease in humans had not been identified. Therefore, there is a substantial unmet need for therapeutic strategies that treat this unrelenting progressive chronic disorder.

Prior to the invention described herein, the pathogenic mechanisms underlying neurodegenerative disorders were complex and largely unknown. Among many factors related to neurodegenerative disorder pathology, microglia and neuroinflammation are thought to be one of the significant originators of this disorder (Sanchez-Guajardo et al. Neuroscience, 2015. 302:47-58). In the context of PD and AD, a predominant deleterious role of activated microglia has been discussed. During the disease progression in brain, resting microglia undergo activation and causes neuroinflammation and neuronal damage directly or via astrocyte activation through the release of toxic molecules including pro-inflammatory cytokines such as tumor necrosis factor-a (TNF-a), interleukin-1α (IL-1α), IL-1β, IL-6 or C1q (Hirsch E C et al. Lancet Neurol, 2009. 8:382-397; Saijo K et al. Cell, 2009. 137:47-59; Farber K et al., J Neurosci Res, 200. 87(3):644-652). By nature, activated microglia and reactive astrocytes are major upstream target for neurodegenerative diseases. Therefore, designing a highly selective agent that can block the microglial activation and shut down the release of toxic molecules without off-target toxicities could produce marked therapeutic effects in neurodegenerative diseases. However, the lack of robust ways to selectively target activated microglia without side effects in the brain hampers this strategy.

Prior to the invention described herein, there was a need for therapies that prevent, stop and/or ameliorate neurodegenerative diseases. Therefore, it is an object of the invention to provide compositions and methods for treating and preventing neurodegenerative diseases without off-target toxicity. It is another object of the invention to provide compositions and methods for blocking or reducing microglial activation in neurodegenerative diseases while leaving normal cells unharmed. It is another object of the invention to provide the compositions and methods for blocking or reducing reactive astrocytes in neurodegenerative diseases while leaving normal cells unharmed. It is another object of the invention to provide the compositions and methods for protecting neurons from activated microglial and/or reactive astrocytes in neurogenerative diseases while leaving normal cells unharmed.

Accordingly, the present invention is based, at least in part, upon the development of compositions and methods for treating Parkinson's disease (PD) and Alzheimer's disease (AD) with long-acting GLP-1r (glucagon-like peptide 1 receptor) agonists with the high bioactivity in the brain. In particular, as described herein, PEGylated forms of GLP-1 analogues (e.g., exenatide) exhibit disease-modifying effects with longer half-lives compared to existing treatments. This allows for less frequent dosing and better patient compliance in treating subjects suffering from or at risk of suffering from PD and/or AD.

The subjects may be suffering from or at risk of suffering from PD or AD in the presence or absence of one or more other non-neurologic conditions. Non-neurologic conditions include type 1 diabetes, type 2 diabetes, proliferative diseases, such as cancer, autoimmune diseases, and other local or systemic diseases such as inflammation and infection.

As described herein, the present invention includes an injectable, e.g., once-weekly or once-monthly, peptide-based drug with disease-modifying effects in PD and AD. Exenatide, an FDA-approved peptide (BYETTA®) and a glucagon-like peptide 1 receptor (GLP-1r) agonist, was recently investigated in a number of PD patients, and results demonstrated improved motor and cognitive symptoms, indicating a potential PD therapy (Aviles-Olmos, I., et al., J Clin Invest, 2013. 123(6): p. 2730-6; Simuni, T. and P. Brundin, J Parkinsons Dis, 2014. 4(3): p. 345-7). As described in detail below, the rationale for applying this glucagon-like peptide 1 receptor (GLP-1r) agonist is based on experimental research demonstrating GLP-1r agonist mediated neuroprotective effects that promote functionally beneficial neuroplasticity in animal models of neurodegeneration. The clinical results of exenatide demonstrate improved motor and cognitive symptoms even one year after the drug was administered (Aviles-Olmos, I., et al., J Clin Invest, 2013. 123(6): p. 2730-6; Simuni, T. and P. Brundin, J Parkinsons Dis, 2014. 4(3): p. 345-7). The ability of exenatide to treat PD is being examined in phase 2 clinical trials. However, exenatide has a short half-life (human t½ is 2 hours or less) and requires twice-daily subcutaneous (s.c.) injections that are inconvenient and difficult for PD patients, especially in advanced stages. The compositions described herein provide similar pharmacological benefits to exenatide in PD with reduced dosing frequency, e.g., a once monthly dosing.

Exenatide (Exendin-4) is a peptide agonist of GLP-1r that facilitates insulin release in type two diabetes (T2D) and is currently on the market as BYETTA® for T2D (Meier, J. J., Nat Rev Endocrinol, 2012. 8(12): p. 728-42). This peptide manages insulin release in a glucose-dependent manner and is therefore safe for non-diabetic patients. Exenatide also reduces a range of neurodegenerative processes (Holscher, C., J Endocrinol, 2014. 221(1): p. T31-41). In preclinical models, exenatide crosses the blood brain barrier (BBB), protects memory formation in AD or motor activity in PD, protects synapses and synaptic functions, enhances neurogenesis, reduces apoptosis, protects neurons from oxidative stress, as well as reduces plaque formation and the chronic inflammation response in the brains of AD and PD mouse models. In a recent clinical trial, moderately advanced PD patients that were treated with exenatide for 12 months showed improved motor and cognitive symptoms and the effects persisted for as long as 12 months after termination of the treatment (Aviles-Olmos, I., et al., J Clin Invest, 2013. 123(6): p. 2730-6; Simuni, T. and P. Brundin, J Parkinsons Dis, 2014. 4(3): p. 345-7).

Short-acting GLP-1r agonists (exenatide and liraglutide) show neuroprotective effects in toxin-based acute animal models of PD and AD (Holscher, C., J Endocrinol, 2014. 221(1): p. T31-41). It should be noted that none of the GLP-1r agonists demonstrate anti-PD efficacy in clinical relevant, genetic α-synuclein associated PD animal models. In AD, short-acting GLP-1r agonists showed neuroprotection properties in toxin-based AD models but its anti-AD effects in genetic AD transgenic (Tg) mice are controversial. For example, liraglutide showed anti-PD efficacy in toxin-based models but failed to demonstrate similar effects in genetic AD Tg mouse models after a long-term treatment (Hansen H H et al., PLoS One. 2016, 11(7):e0158205). Generally, compounds with proven efficacy only in toxin-induced neurodegenerative disease models have often failed in clinical trials. Recently, it has been reported that liraglutide failed to change cognitive scores in AD patients after a long-term treatment. Together, this implies that an alternative GLP-1r agonist with a strong therapeutic efficacy in clinically relevant models associated with PD (α-synuclein PD phenotypes) or AD (amyloid and tau phenotypes) pathobiology is needed to warrant successful clinical trials in patients. The compositions described herein provide strong anti-PD and anti-AD therapeutic efficacies of a long-acting GLP-1r agonist in α-synuclein associated PD models and 3×Tg-AD models that are considered to represent close models of the neurodegenerative process of PD and AD, respectively.

Exenatide, like other peptide drugs, is inherently short-lived and unstable in the blood stream and therefore require frequent injections. Although PEGylation is a gold standard method to extend the half-life of protein drugs (Harris, J. M. and R. B. Chess, Nat Rev Drug Discov, 2003. 2(3): p. 214-21), it is generally not applied to smaller peptide drugs, because conjugation with a large PEG molecule often diminishes the biological activity of the peptide (e.g., to less than 1% biological activity vs. native peptide). As described in detail herein, to empower potent and long-acting peptides, a unique PEGylation technology was developed that extends circulating half-lives of short-acting peptides while simultaneously preserving therapeutic activities of exenatide (patent publications WO2013002580 and US20130217622, incorporated herein by reference). NLY001 is a long-acting form of exenatide using this PEGylation technology and is being investigated as a once-weekly, bi-monthly or once-monthly T2D treatment (FIG. 1), with promising results compared to other GLP-1r agonists on the market.

NLY001, as a long-acting PEGylated form of exenatide, has an extended half-life (88 hours in primates). The long-acting features of NLY001 are engineered through a unique half-life extension technology which still allows the composition to follow the same target and mechanism of action as exenatide. A peptide agonist of GLP-1r, exenatide delays numerous neurodegenerative processes (Holscher, C., J Endocrinol, 2014. 221(1): p. T31-41) in addition to facilitating insulin release in T2D patients by stimulating GLP-1r. This peptide manages insulin release in a glucose-dependent manner and is therefore safe for non-diabetic patients.

As a long-acting exenatide-based therapy, NLY001 offers an improved drug delivery approach compared to exenatide, while maintaining its pharmacological effects. For example, as described in detail below, similar to exenatide, NLY001 improves motor and cognitive symptoms in PD. Unlike exenatide therapies identified prior to the invention described herein, NLY001 is delivered to patients with a single or bi-monthly injection, preventing daily multiple injections and improving compliance to therapy.

Because NLY001 has a large molecular weight poly (ethylene glycol) polymer (PEG, 50,000 Da) conjugated to the small exenatide peptide (4,000 Da), similar pharmacological efficacy to exenatide in PD and AD was completely unexpected because of the likely inability to cross the blood-brain barrier (BBB) (Pardridge, W. M., NeuroRx, 2005. 2(1): p. 3-14). As described in detail below, it was unexpectedly discovered that subcutaneously-administered NLY001 accumulates significantly higher in the brain of PD and AD animal models and demonstrates clear beneficial effects in a number of newly established PD animal models (see also, Luk, K. C., et al., Science, 2012. 338(6109): p. 949-53) and AD animal models. As described in detail below, the results demonstrate that the administration of NLY001 protects against alpha-synuclein preformed fibrils (PFFs)-induced loss of dopaminergic neurons, reduces the PFF-induced Lewy Body-like pathology, inhibits the PFF-induced reduction in striatal dopamine terminal density, and restores the behavioral deficits induced by PFFs as well as increases lifespan of Tg PD models. Importantly, NLY001 significantly blocked microglia activation and decreased the formation of reactive astrocytes in the brain. Taken together, the findings described in detail below clearly indicate that NLY001 has beneficial neuroprotective/disease-modifying effects against alpha-synuclein PFFs-induced behavioral deficits. Similarly, in Tg AD models, NLY001 treatment ameliorated memory impairment and reduced amyloid aggregation and tau formation, the hallmark of AD. Consistent with PD studies, NLY001 demonstrated significantly inhibited microglia activation and the population of reactive astrocytes in the AD brain.

Anti-PD efficacies of long-acting GLP-1r agonists like GLP-1 peptide analogs carrying a large molecular weight half-life extension carrier, were previously unknown. The findings described herein demonstrate anti-PD and anti-AD effects of long-acting GLP-1r agonist in a number of complementary animal models (preformed on fibrils-induced α-synucleinopathy PD mouse models, A53T α-synuclein Tg mouse models and 3×Tg AD mouse models) and ellucidates mechanisms of action. Long-acting exenatide revolutionizes PD and AD therapy coupled with greatly improved patient compliance—a once weekly or monthly treatment option. Introducing an exenatide-based therapy with significantly less frequent injections is an effective treatment option for affected patients and families.

The pathogenesis of PD is due to: 1) neuroinflammation and neurotoxicity induced by activated microglia and reactive astrocytes, 2) mitochondria dysfunction, 3) synaptic dysfunction, and 4) lower levels of neurotrophic factor. Although the mechanisms of neuroprotective action of exenatide are uncertain, growing evidence suggests that it regulates/delays some or all of these processes contributing to the neurodegenerative process of PD. Therefore, as described in detail below, NLY001 confers beneficial neuroprotective effects in these pathways as well. As described below, the newly established preformed fibrils (PFFs) of α-synuclein PD mouse model and A53T Tg PD mouse model exhibit abnormal levels of reactive oxygen species (ROS) leading to an increase of oxidative stress and subsequently mitochondria dysfunction, and recapitulates PD like Lewy bodies (LBs) pathology through a cell-to-cell transmission pathway. All of these processes contribute to the disease process of PD. As described in detail herein, since administration of NLY001 into tow complementary mouse models of PD protects against the α-synuclein-associated PD pathology, NLY001 is engaged in and manipulates these pathways as well.

The etiology of neurodegenerative diseases including PD and AD is largely now well defined. There is evidence for increased immune activation in neurodegenerative diseases. Most research focused on the role of microglia and astrocytes, the resident innate immune cells of the brain on PD and AD pathology (Sanchez-Guajardo V et al. Neuroscience. 2015. 302:47-58, Perry V H et al., Nat Rev Neurol. 2014. 10:217-224). In response to neurodegeneration and the accumulation of abnormally aggregated proteins, such as α-synuclein and β-amyloid, resting microglia become an activated state and release various cytokines and neurotoxic molecules including TNF-α, IL-1α, IL-1β, IL-6, and C1q that drive their proliferation and activate astrocytes (A1 astrocytes). Consequently, such inflammatory mediators released from activated microglia or reactive astrocytes, induced by activated microglia, causes neuronal damage and contribute to the progression of neurodegenerative diseases. Therefore, activated microglia can be described as major upstream bad actors in neurodegenerative diseases. Inhibition of microglia activation without off-target toxicity is a logical strategy to prevent, stop and/or reverse the neurodegeneration process. However, prior to the invention described herein, the lack of translational methods to specifically target microglia activation hampered this strategy. For example, clinical trials of various anti-inflammatory agents including NSAIDs (de Jong D et al. PLoS ONE. 2008. 23:e1475), rosiglitazone (Gold M et al. Dement Geriatr Cogn Disord. 2010. 30:131-146), statins (Feldman H H et al. Neurology. 2010. 74:956-964) and prednisone (Aisen P S et al. Neurology. 2000. 54:588-593), have failed to slow down the progression of AD. Disappointing clinical trial results may be due to limited BBB permeability and/or inadequate suppression of key proinflammatory and neurotoxic cytokines.

The studies describe a unique strategy to selectively target and block microglia and astrocytes activation and the release of inflammatory and neurotoxic molecules from activated resident innate immune cells; thus prevent, stop and/or ameliorate the progression of neurodegenerative diseases. Unexpectedly, it was discovered that microglia activated by abnormally aggregated proteins upregulate GLP-1r and a long-acting GLP-1r agonist bound to activated microglia significantly inhibit the release of toxic molecules including TNF-α, IL-1α, IL-1β, IL-6, and C1q and protect neurons. Surprisingly, through GLP-1r internalization assay, it was discovered that a long-acting GLP-1r agonist demonstrates slow internalization of GLP-1r, reduces the rate of GLP-1r recycling compared to that of short-acting GLP-1r agonists (exenatide and liraglutide), thus can continuously activate GLP-1r and induce GLP-1r signaling in the brain. Patients treated with a short-acting GLP-1r agonist would experience "off time" that will mar the therapeutic effect during a chronic treatment. In contrast, NLY001 has the ability to penetrate BBB and activate GLP-1r in the brain in a continuous fashion without "off time" and without off-target toxicity. Such unique property of a long-acting GLP-1r agonist is critical to maximize synergistic anti-inflammatory and neuroprotection properties of GLP-1r agonist in neurodegenerative diseases.

Parkinson's Disease

Parkinson's disease (PD, also known as idiopathic or primary parkinsonism, hypokinetic rigid syndrome (HRS), or paralysis agitans) is a degenerative disorder of the central nervous system mainly affecting the motor system. The motor symptoms of Parkinson's disease result from the death of dopamine-generating cells in the substantia nigra, a region of the midbrain. The causes of this cell death are poorly understood. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease, and depression is the most common psychiatric symptom. Other symptoms include sensory, sleep and emotional problems. Parkinson's disease is more common in older people, with most cases occurring after the age of 50; when it is seen in young adults, it is called young onset PD (YOPD).

The main motor symptoms are collectively called "parkinsonism," or a "parkinsonian syndrome." The disease can be either primary or secondary. Primary Parkinson's disease is referred to as idiopathic (having no known cause), although some atypical cases have a genetic origin, while secondary parkinsonism is due to known causes like toxins. The pathology of the disease is characterized by the accumulation of a protein into Lewy bodies in neurons, and insufficient formation and activity of dopamine in certain parts of the midbrain. Where the Lewy bodies are located is often related to the expression and degree of the symptoms of an individual. Diagnosis of typical cases is mainly based on symptoms, with tests such as neuroimaging being used for confirmation.

Diagnosis of Parkinson's disease involves a physician taking a medical history and performing a neurological examination. There is no lab test that will clearly identify the disease, but brain scans are sometimes used to rule out disorders that could give rise to similar symptoms. People may be given levodopa and resulting relief of motor impairment tends to confirm diagnosis. The finding of Lewy bodies in the midbrain on autopsy is usually considered proof that the person had Parkinson's disease. The progress of the illness over time may reveal it is not Parkinson's disease, and some authorities recommend that the diagnosis be periodically reviewed. Other causes that can secondarily produce a parkinsonian syndrome are Alzheimer's disease, multiple cerebral infarction and drug-induced parkinsonism. Parkinson plus syndromes such as progressive supranuclear palsy and multiple system atrophy must be ruled out. Anti-Parkinson's medications are typically less effective at controlling symptoms in Parkinson plus syndromes. Faster progression rates, early cognitive dysfunction or postural instability, minimal tremor or symmetry at onset may indicate a Parkinson plus disease rather than PD itself. Genetic forms are usually classified as PD, although the terms familial Parkinson's disease and familial parkinsonism are used for disease entities with an autosomal dominant or recessive pattern of inheritance.

The PD Society Brain Bank criteria require slowness of movement (bradykinesia) plus either rigidity, resting tremor, or postural instability. Other possible causes for these symptoms need to be ruled out prior to diagnosis with PD. Finally, three or more of the following features are required during onset or evolution: unilateral onset, tremor at rest, progression in time, asymmetry of motor symptoms, response to levodopa for at least five years, clinical course of at least ten years and appearance of dyskinesias induced by the intake of excessive levodopa. Accuracy of diagnostic criteria evaluated at autopsy is 75-90%, with specialists such as neurologists having the highest rates. Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, diffusion MRI, has been reported to be useful at discriminating between typical and atypical parkinsonism, although its exact diagnostic value is still under investigation. Dopaminergic function in the basal ganglia can be measured with different PET and SPECT radiotracers. Examples are ioflupane (123I) (trade name DaTSCAN) and iometopane (Dopascan) for SPECT or fluorodeoxyglucose (18F) and DTBZ for PET. A pattern of reduced dopaminergic activity in the basal ganglia can aid in diagnosing PD.

Treatments, typically the medications L-DOPA and dopamine agonists, improve the early symptoms of the disease. As the disease progresses and dopaminergic neurons continue to be lost, these drugs eventually become ineffective at treating the symptoms and at the same time produce a complication marked by involuntary writhing movements. Surgery and deep brain stimulation have been used to reduce motor symptoms as a last resort in severe cases where drugs are ineffective. Although dopamine replacement alleviates the symptomatic motor dysfunction, its effectiveness is reduced as the disease progresses, leading to unacceptable side effects such as severe motor fluctuations and dyskinesias. Furthermore, there is no therapy that will halt the progress of the disease (Lang, A. E. and A. M. Lozano, N Engl J Med, 1998. 339(15): p. 1044-53; Lang, A. E. and A. M. Lozano, N Engl J Med, 1998. 339(16): p. 1130-43). Moreover, this palliative therapeutic approach does not address the underlying mechanisms of the disease (Nagatsua, T. and M. Sawadab, Parkinsonism Relat Disord, 2009. 15 Suppl 1: p. S3-8).

The term parkinsonism is used for a motor syndrome whose main symptoms are tremor at rest, stiffness, slowing of movement and postural instability. Parkinsonian syndromes can be divided into four subtypes according to their origin: primary or idiopathic, secondary or acquired, hereditary parkinsonism, and Parkinson plus syndromes or multiple system degeneration. Usually classified as a movement disorder, PD also gives rise to several non-motor types of symptoms such as sensory deficits, cognitive difficulties or sleep problems. Parkinson plus diseases are primary parkinsonisms which present additional features. They include multiple system atrophy, progressive supranuclear palsy, corticobasal degeneration and dementia with Lewy bodies.

In terms of pathophysiology, PD is considered a synucleiopathy due to an abnormal accumulation of alpha-synuclein protein in the brain in the form of Lewy bodies, as opposed to other diseases such as Alzheimer's disease where the brain accumulates tau protein in the form of neurofibrillary tangles. Nevertheless, there is clinical and pathological overlap between tauopathies and synucleinopathies. The most typical symptom of Alzheimer's disease, dementia, occurs in advanced stages of PD, while it is common to find neurofibrillary tangles in brains affected by PD. Dementia with Lewy bodies (DLB) is another synucleinopathy that has similarities with PD, and especially with the subset of PD cases with dementia. However, the relationship between PD and DLB is complex and still has to be clarified. They may represent parts of a continuum or they may be separate diseases.

Mutations in specific genes have been conclusively shown to cause PD. These genes code for alpha-synuclein (SNCA), parkin (PRKN), leucine-rich repeat kinase 2 (LRRK2 or dardarin), PTEN-induced putative kinase 1 (PINK1), DJ-1 and ATP13A2. In most cases, people with these mutations will develop PD. With the exception of LRRK2, however, they account for only a small minority of cases of PD. The most extensively studied PD-related genes are SNCA and LRRK2. Mutations in genes including SNCA, LRRK2 and glucocerebrosidase (GBA) have been found to be risk factors for sporadic PD. Mutations in GBA are known to cause Gaucher's disease. Genome-wide association studies, which search for mutated alleles with low penetrance in sporadic cases, have now yielded many positive results.

The role of the SNCA gene is important in PD because the alpha-synuclein protein is the main component of Lewy bodies. The histopathology (microscopic anatomy) of the substantia nigra and several other brain regions shows neuronal loss and Lewy bodies in many of the remaining nerve cells. Neuronal loss is accompanied by death of astrocytes (star-shaped glial cells) and activation of the microglia (another type of glial cell). Lewy bodies are a key pathological feature of PD.

Alzheimer's Disease

Alzheimer's disease (AD) accounts for 60% to 70% of cases of dementia. It is a chronic neurodegenerative disease that often starts slowly, but progressively worsens over time. The most common early symptom is short-term memory loss. As the disease advances, symptoms include problems with language, mood swings, loss of motivation, disorientation, behavioral issues, and poorly managed self-care. Gradually, bodily functions are lost, ultimately leading to death. Although the speed of progression can vary, the average life expectancy following diagnosis is three to nine years. The cause of Alzheimer's disease is poorly understood. About 70% of the risk is believed to be genetic with many genes involved. Other risk factors include a history of head injuries, hypertension, or depression. The disease process is associated with plaques and tangles in the brain.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Alzheimer's disease has been hypothesized to be a protein misfolding disease (proteopathy), caused by accumulation of abnormally folded A-beta and tau proteins in the brain. Plaques are made up of small peptides, 39-43 amino acids in length, called beta-amyloid (also written as A-beta or A(3). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques.

A probable diagnosis is based on the history of the illness and cognitive testing with medical imaging and blood tests to rule out other possible causes. Initial symptoms are often mistaken for normal ageing. Examination of brain tissue is needed for a definite diagnosis. Alzheimer's disease is diagnosed through a complete medical assessment. There is no one clinical test that can determine whether a person has Alzheimer's. Usually several tests are performed to rule out any other cause of dementia. The only definitive method of diagnosis is examination of brain tissue obtained from a biopsy or autopsy. Tests (such as blood tests and brain imaging) are used to rule out other causes of dementia-like symptoms. Laboratory tests and screening include: complete blood cell count; electrolyte panel; screening metabolic panel; thyroid gland function tests; vitamin B-12 folate levels; tests for syphilis and, depending on history, for human immunodeficiency antibodies; urinalysis; electrocardiogram (ECG); chest X-ray; computerized tomography (CT) head scan; and an electroencephalogram (EEG). A lumbar puncture may also be informative in the overall diagnosis.

There are no medications or supplements that decrease risk. No treatments stop or reverse its progression, though some may temporarily improve symptoms.

GLP-1 Agonists (e.g., Exenatide)

Exenatide (marketed as BYETTA®, Bydureon) is a glucagon-like peptide-1 agonist (GLP-1 agonist) medication, belonging to the group of incretin mimetics, approved in April 2005 for the treatment of diabetes mellitus type 2. Exenatide in its BYETTA® form is administered as a subcutaneous injection (under the skin) of the abdomen, thigh, or arm, any time within the 60 minutes before the first and last meal of the day. A once-weekly injection has been approved as of Jan. 27, 2012 under the trademark Bydureon. It is manufactured by Amylin Pharmaceuticals and commercialized by Astrazeneca.

Exenatide is a synthetic version of Exendin-4, a hormone found in the saliva of the Gila monster. It displays biological properties similar to human glucagon-like peptide-1 (GLP-1), a regulator of glucose metabolism and insulin secretion. According to the package insert, exenatide enhances glucose-dependent insulin secretion by the pancreatic beta-cell, suppresses inappropriately elevated glucagon secretion, and slows gastric emptying, although the mechanism of action is still under study.

Exenatide is a 39-amino-acid peptide, an insulin secretagogue, with glucoregulatory effects. The peptide sequence of exenatide is: H(His)G(Gly)E(Glu)G(Gly)T(Thr)F(Phe)T (Thr) S(Ser)D(Asp)L(Leu)S(Ser)K(Lys)Q(Gln)M(Met)E (Glu)E(Glu)E(Glu)A(Ala)V(Val)R(Arg)L(Leu) F(Phe)I(Ile) E(Glu)W(Trp)L(Leu)K(Lys)N(Asn)G(Gly)G(Gly)P(Pro)S (Ser)S(Ser)G(Gly)A(Ala) P(Pro)P(Pro)P(Pro)S(Ser)(SEQ ID NO: 1). Exenatide was approved by the FDA on Apr. 28, 2005 for patients whose diabetes was not well-controlled on other oral medication. The medication is injected subcutaneously twice per day using a filled pen-like device.

The incretin hormones GLP-1 and glucose-dependent insulinotropic peptide (GIP) are produced by the L and K endocrine cells of the intestine following ingestion of food. GLP-1 and GIP stimulate insulin secretion from the beta cells of the islets of Langerhans in the pancreas. Only GLP-1 causes insulin secretion in the diabetic state; however, GLP-1 itself is ineffective as a clinical treatment for diabetes as it has a very short half-life in vivo. Exenatide bears a 50% amino acid homology to GLP-1 and it has a longer half-life in vivo. Thus, it was tested for its ability to stimulate insulin secretion and lower blood glucose in mammals, and was found to be effective in the diabetic state. In studies on rodents, it has also been shown to increase the number of beta cells in the pancreas.

Commercially, exenatide is produced by direct chemical synthesis. Historically, exenatide was discovered as Exendin-4, a protein naturally secreted in the saliva and concentrated in the tail of the Gila monster. Exendin-4 shares extensive homology and function with mammalian GLP-1, but has a therapeutic advantage in its resistance to degradation by DPP-IV (which breaks down GLP-1 in mammals) therefore allowing for a longer pharmacological half-life. The biochemical characteristics of Exendin-4 enabled consideration and development of exenatide as a diabetes mellitus treatment strategy. Subsequent clinical testing led to the discovery of the also desirable glucagon and appetite-suppressant effects.

In its twice daily BYETTA® form, exenatide raises insulin levels quickly (within about ten minutes of administration) with the insulin levels subsiding substantially over the next hour or two. A dose taken after meals has a much smaller effect on blood sugar than one taken beforehand. The effects on blood sugar diminish after six to eight hours. In its BYETTA® form, the medicine is available in two doses: 5 mcg. and 10 mcg. Treatment often begins with the 5 mcg. dosage, which is increased if adverse effects are not significant. Its once weekly Bydureon form is unaffected by the time between the injection and when meals are taken. Bydureon has the advantage of providing 24-hour coverage for blood sugar lowering, while BYETTA® has the advantage of providing better control of the blood sugar spike that occurs right after eating. Per the FDA label for Bydureon, Bydureon lowers HbA1c blood sugar by an average of 1.6%, while BYETTA® lowers it by an average of 0.9%. Both BYETTA® and Bydureon have similar weight loss benefits. Per the FDA approved Bydureon label, the levels of nausea are lower for Bydureon patients than for BYETTA® patients.

In some embodiments, the present invention is based using on other (non-exenatide) types of long-acting GLP-1 agonists to treat PD and AD. In some cases, the long-acting GLP-1 agonist comprises an Fc-fusion GLP-1 (e.g. dulaglutide, efpeglenatide) or derivative thereof. In some cases, the long-acting GLP-1 agonist comprises an albumin-fusion GLP-1 (e.g. albiglutide) or derivative thereof. An example of an Fc-fusion GLP-1 composition used to treat PD or AD is dulaglutide. Dulaglutide is a glucagon-like peptide 1 receptor agonist (GLP-1 agonist) for the treatment of type 2 diabetes that can be used once weekly. Dulaglutide consists of GLP-1(7-37) covalently linked to an Fc fragment of human IgG4, thereby protecting the GLP-1 moiety from inactivation by dipeptidyl peptidase 4. GLP-1 is a hormone that is involved in the normalization of level of glucose in blood (glycemia). GLP-1 is normally secreted by L cells of the gastrointestinal mucosa in response to a meal. Dulaglutide binds to glucagon-like peptide 1 receptors, slowing gastric emptying and increases insulin secretion by pancreatic Beta cells. Simultaneously the compound reduces the elevated glucagon secretion by inhibiting alpha cells of the pancreas, which is known to be inappropriate in the diabetic patient. An example of an albumin-fusion of GLP-1 composition used to treat PD or AD is albiglutide. Albiglutide is a glucagon-like peptide-1 agonist (GLP-1 agonist) drug used for treatment of type 2 diabetes. It is a dipeptidyl peptidase-4-resistant glucagon-like peptide-1 dimer fused to human albumin. Albiglutide has a half-life of four to seven days.

Polyethylene Glycol (PEG)

Polyethylene glycol (PEG) is a polyether compound with many applications from industrial manufacturing to medicine. The structure of PEG is (note the repeated element in parentheses): H—(O—CH2-CH2)n-OH PEG is also known as polyethylene oxide (PEO) or polyoxyethylene (POE), depending on its molecular weight. PEG, PEO, or POE refers to an oligomer or polymer of ethylene oxide. The three names are chemically synonymous, but historically PEG is preferred in the biomedical field, whereas PEO is more prevalent in the field of polymer chemistry. Because different applications require different polymer chain lengths, PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. Very high purity PEG has recently been shown to be crystalline, allowing determination of a crystal structure by x-ray diffraction. Since purification and separation of pure oligomers is difficult, the price for this type of quality is often 10-1000 fold that of polydisperse PEG.

PEGs are also available with different geometries. Branched PEGs have three to ten PEG chains emanating from a central core group. Star PEGs have 10 to 100 PEG chains emanating from a central core group. Comb PEGs have multiple PEG chains normally grafted onto a polymer backbone. The numbers that are often included in the names of PEGs indicate their average molecular weights (e.g. a PEG with n=9 would have an average molecular weight of approximately 400 daltons, and would be labeled PEG 400. Most PEGs include molecules with a distribution of molecular weights (i.e. they are polydisperse). The size distribution can be characterized statistically by its weight average molecular weight (Mw) and its number average molecular weight (Mn), the ratio of which is called the polydispersity index (Mw/Mn). MW and Mn can be measured by mass spectrometry.

PEGylation is the act of covalently coupling a PEG structure to another larger molecule, for example, a therapeutic protein, which is then referred to as a PEGylated protein. PEGylated interferon alfa-2a or -2b are commonly used injectable treatments for Hepatitis C infection. PEG is soluble in water, methanol, ethanol, acetonitrile, benzene, and dichloromethane, and is insoluble in diethyl ether and hexane. It is coupled to hydrophobic molecules to produce non-ionic surfactants. PEGs contain potential toxic impurities, such as ethylene oxide and 1,4-dioxane. Ethylene Glycol and its ethers are nephrotoxic if applied to damaged skin.

Polyethylene glycol (PEG) and related polymers (PEG phospholipid constructs) are often sonicated when used in biomedical applications. However, PEG is very sensitive to sonolytic degradation and PEG degradation products can be toxic to mammalian cells. It is, thus, imperative to assess potential PEG degradation to ensure that the final material does not contain undocumented contaminants that can introduce artifacts into experimental results.

PEGs and methoxypolyethylene glycols vary in consistency from liquid to solid, depending on the molecular weight, as indicated by a number following the name. They are used commercially in numerous applications, including as surfactants, in foods, in cosmetics, in pharmaceutics, in biomedicine, as dispersing agents, as solvents, in ointments, in suppository bases, as tablet excipients, and as laxatives. Some specific groups are lauromacrogols, nonoxynols, octoxynols, and poloxamers.

Polyethylene glycol is produced by the interaction of ethylene oxide with water, ethylene glycol, or ethylene glycol oligomers. The reaction is catalyzed by acidic or basic catalysts. Ethylene glycol and its oligomers are preferable as a starting material instead of water, because they allow the creation of polymers with a low polydispersity (narrow molecular weight distribution). Polymer chain length depends on the ratio of reactants.

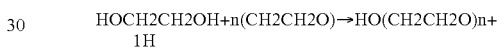

Depending on the catalyst type, the mechanism of polymerization can be cationic or anionic. Polymerization of ethylene oxide is an exothermic process.

Polyethylene oxide, or high-molecular weight polyethylene glycol, is synthesized by suspension polymerization. It is necessary to hold the growing polymer chain in solution in the course of the polycondensation process. The reaction is catalyzed by magnesium-, aluminium-, or calcium-organoelement compounds. To prevent coagulation of polymer chains from solution, chelating additives such as dimethylglyoxime are used. Alkali catalysts such as sodium hydroxide (NaOH), potassium hydroxide (KOH), or sodium carbonate (Na2CO3) are used to prepare low-molecular-weight polyethylene glycol.

PEG is used as an excipient in many pharmaceutical products. Lower-molecular-weight variants are used as solvents in oral liquids and soft capsules, whereas solid variants are used as ointment bases, tablet binders, film coatings, and lubricants. PEG is also used in lubricating eye drops.

Polyethylene glycol has a low toxicity and is used in a variety of products. The polymer is used as a lubricating coating for various surfaces in aqueous and non-aqueous environments. Since PEG is a flexible, water-soluble polymer, it can be used to create very high osmotic pressures (on the order of tens of atmospheres). It also is unlikely to have specific interactions with biological chemicals. These properties make PEG one of the most useful molecules for applying osmotic pressure in biochemistry and biomembranes experiments, in particular when using the osmotic stress technique.

PEGylation (also often styled pegylation) is the process of both covalent and non-covalent attachment or amalgamation of polyethylene glycol (PEG) polymer chains to molecules and macrostructures, such as a drug, therapeutic protein or vesicle, which is then described as PEGylated (pegylated). PEGylation is routinely achieved by incubation of a reactive derivative of PEG with the target molecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

PEGylation is the process of attaching the strands of the polymer PEG to molecules, most typically peptides, proteins, and antibody fragments, that can improve the safety and efficiency of many therapeutics. It produces alterations in the physiochemical properties including changes in conformation, electrostatic binding, hydrophobicity etc. These physical and chemical changes increase systemic retention of the therapeutic agent. Also, it can influence the binding affinity of the therapeutic moiety to the cell receptors and can alter the absorption and distribution patterns.

PEG is a particularly attractive polymer for conjugation. The specific characteristics of PEG moieties relevant to pharmaceutical applications are: water solubility, high mobility in solution, lack of toxicity and low immunogenicity, ready clearance from the body, and altered distribution in the body.

PEGylation Process

The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The overall PEGylation processes for protein conjugation can be broadly classified into two types, namely a solution phase batch process and an on-column fed-batch process. The simple and commonly adopted batch process involves the mixing of reagents together in a suitable buffer solution, preferably at a temperature between 4° and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers. The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc. made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. Third generation pegylation agents, where the shape of the polymer has been branched, Y shaped or comb shaped are available which show reduced viscosity and lack of organ accumulation. Unpredictability in clearance times for PEGylated compounds may lead to the accumulation of large molecular weight compounds in the liver leading to inclusion bodies with no known toxicologic consequences. Furthermore, alteration in the chain length may lead to unexpected clearance times in vivo.

PEGylation of GLP-1r Agonist (NLY001, PB-119, LY2428757)

As described below, the yield of an Exendin-4 analogue (e.g., exenatide) or GLP-1 analogue can be increased via the selective PEGylation and treatment effect of medications can be increased. Such technology increases molecular weight, defense of a metabolism site and inhibition of an immunogenicity site, increasing in vivo half-life and stability and reducing immunogenicity. Furthermore, kidney excretion of peptides and proteins bound with PEG is reduced due to the increase of molecular weights of peptides and proteins by PEG, so that PEGylation has advantages of increasing effects in both pharmacokinetically and pharmacodynamically.

Also, the polyethylene glycol or a derivative thereof according to the present invention is a linear type or a branched type, and for the branched type, preferably a dimeric type or a trimeric type may be used, and more preferably a trimeric type may be used. Specifically, the polyethylene glycol derivative is, for example, methoxypolyethylene glycol succinimidylpropionate, methoxypolyethylene glycol N-hydroxysuccinimide, methoxypolyethylene glycol propionaldehyde, methoxypolyethylene glycol maleimide, or multiple branched types of these derivatives. Preferably, the polyethylene glycol derivative is linear methoxypolyethylene glycol maleimide, branch type methoxypolyethylene glycol maleimide or trimeric methoxypolyethylene glycol maleimide, and more preferably is trimeric methoxypolyethylene glycol maleimide.

As described herein, after the Exendin-4 analogue (e.g., exenatide) is PEGylated with polyethylene glycol or the derivative thereof is prepared, the molecular structure of the analogue may be confirmed by a mass spectroscope, a liquid chromatography, an X-ray diffraction analysis, a polarimetry, and comparison between calculated values and measured values of representative elements constituting the PEGylated exenatide.

When the composition of the present invention is used as medication, the pharmaceutical composition containing the Exendin-4 analogue (e.g., exenatide) PEGylated with polyethylene glycol or a derivative thereof may be administrated after being formulated into various oral or non-oral administration forms as the following in case of clinical administration, but is not limited thereof.

For oral administration purposed formulation, for example, there are tablets, pellets, hard/soft capsules, liquids, suspensions, emulsifiers, syrups, granules, elixirs, troches, etc., and these formulations include diluents (example: lactose, dextrose, sucrose, mannitol, sorbitol, cellulose and/or glycine), slip modifiers (example: silica, talc, stearate and its magnesium or calcium salt and/or polyethylene glycol) in addition to the active ingredient. Tablets may also include binders such as magnesium aluminum silicate, starch paste, gelatin, methyl cellulose, sodium carboxymethyl cellulose and/or polyvinyl pyrrolidine, and may include disintegrating agents such as starch, agar, alginic acid or sodium salt thereof or boiling mixture and/or absorbents, coloring agents, flavoring agents and sweetening agents if needed.

The pharmaceutical composition containing the Exendin-4 analogue PEGylated with polyethylene glycol or a derivative thereof may be non-orally administrated, and the administration is done by subcutaneous injection, intravenous injection, intramuscular injection, intrathoracic injection, or topical administration.

The Exendin-4 analogue (e.g., exenatide) PEGylated with polyethylene glycol or a derivative thereof may be prepared as a liquid or suspension by having mixed it with stabilizer or buffer in water to formulize it into non-orally administration purposed formulation, and this may be prepared into ampoule or vial unit administration form. The composition is sterilized and/or may include adjuvants such as antiseptics, stabilizers, hydrators or emulsify stimulators, osmotic pressure controlling purposed salts and/or buffers, and other substances beneficial for treatments, and may be formulated according to traditional methods of mixture, granulation or coating.

The human body dose of the pharmaceutical composition containing the Exendin-4 analogue (e.g., exenatide) PEGylated with polyethylene glycol or a derivative thereof according to the present invention may vary depending on the age, body weight, gender, administration form, health status and level of disease of patients, and may be administrated via oral or non-oral route following decisions of doctors or pharmacists with preferably dose of 0.01 to 200 mg/kg/day.

Blood Brain Barrier (BBB)

The blood-brain barrier (BBB) is a highly selective permeability barrier that separates the circulating blood from the brain extracellular fluid (BECF) in the central nervous system (CNS). The blood-brain barrier is formed by brain endothelial cells, which are connected by tight junctions with an extremely high electrical resistivity. Astrocytes are necessary to create the blood-brain barrier. The blood-brain barrier allows the passage of lipid-soluble molecules, water, and some gases by passive diffusion, as well as the selective transport of molecules such as amino acids and glucose which are crucial to neural function. The blood-brain barrier occurs along all brain capillaries and consists of tight junctions around the capillaries that do not exist in normal circulation. Endothelial cells restrict the diffusion of microscopic objects (e.g., bacteria) and large or hydrophilic molecules into the cerebrospinal fluid (CSF), while allowing the diffusion of small hydrophobic molecules (e.g., O2, CO2, hormones). Cells of the barrier actively transport metabolic products such as glucose across the barrier with specific proteins.

This "barrier" results from the selectivity of the tight junctions between endothelial cells in CNS vessels that restricts the passage of solutes. At the interface between blood and the brain, endothelial cells are stitched together by these tight junctions, which are composed of smaller subunits, frequently biochemical dimers, that are transmembrane proteins such as occludin, claudins, junctional adhesion molecule (JAM), or ESAM, for example. Each of these transmembrane proteins is anchored into the endothelial cells by another protein complex that includes zo-1 and associated proteins.

The blood-brain barrier is formed by the brain capillary endothelium and excludes from the brain ~100% of large-molecule neurotherapeutics and more than 98% of all small-molecule drugs. Overcoming the difficulty of delivering therapeutic agents to specific regions of the brain presents a major challenge to treatment of most brain disorders. In its neuroprotective role, the blood-brain barrier functions to hinder the delivery of many potentially important diagnostic and therapeutic agents to the brain. Therapeutic molecules and antibodies that might otherwise be effective in diagnosis and therapy do not cross the BBB in adequate amounts. Mechanisms for drug targeting in the brain involve going either "through" or "behind" the BBB. Modalities for drug delivery/Dosage form through the BBB entail its disruption by osmotic means; biochemically by the use of vasoactive substances such as bradykinin; or even by localized exposure to high-intensity focused ultrasound (HIFU). Other methods used to get through the BBB may entail the use of endogenous transport systems, including carrier-mediated transporters such as glucose and amino acid carriers; receptor-mediated transcytosis for insulin or transferrin; and the blocking of active efflux transporters such as p-glycoprotein. However, vectors targeting BBB transporters, such as the transferrin receptor, have been found to remain entrapped in brain endothelial cells of capillaries, instead of being ferried across the BBB into the cerebral parenchyma. Methods for drug delivery behind the BBB include intracerebral implantation (e.g., using needles) and convection-enhanced distribution. Additionally, mannitol can be used in bypassing the BBB.

It is well known that peptide or protein biological drugs without the ability to target blood-brain barrier receptors, such as the transferrin receptor, do not cross the BBB. Due to the high molecular weight of PEGylated exenatide analogue or GLP-1 analogue and lack of ligands that target blood-brain barrier receptors, it was unexpected that the compositions described herein would cross the blood brain barrier and treat PD and AD.

This invention is further illustrated by the following examples which should not be construed as limiting. The contents of all references, patents, and published patent applications cited throughout this application, as well as the figures, are incorporated herein by reference.

EXAMPLES

Example 1: Activated Microglia Upregulate GLP-1r and Agonists of GLP-1r Selectively Blocks Microglial Activation and Inhibits the Release of Multiple Neurotoxic Molecules Activated microglia are one of the originators of neurodegenerative diseases. Microglial activation leads to an enhanced production of pro-inflammatory and neurotoxic mediators such as TNF-α, IL-1α, IL-1β, IL-6, and C1q. As a result, these inflammatory mediators directly or via astrocyte activation induce neuro-inflammation and neuronal damage. For instance, TNF-α is expressed at very low levels by a variety of brain cells including neurons, but when microglia and astrocytes are activated by pathogens or damage, express and release high levels of TNF-α. It has been reported that TNF-α produced by activated microglia is necessary and sufficient to trigger apoptosis in neuronal cells (Guadagno J et al. Cell Death and Disease. 2013. 4:e538), and there is evidence that TNF-α contribute to a variety of brain pathologies such as PD, AD, multiple sclerosis and other neurodegenerative diseases. Prior to the invention described herein, no clinically tested robust methods have existed to selectively target and affect microglial and astrocyte activation in humans.

Results

Figure 2A:
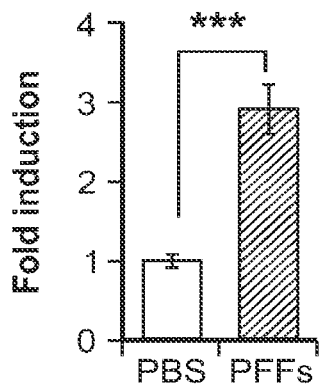
FIGS. 2A-2C are bar graphs showing mRNA GLP-1r expression profiles in (FIG. 2A); α-synuclein PFFs-activated primary microglial cells (n=4) and human post-mortem brain tissues from healthy and patients with (FIG. 2B); and Parkinson's disease (n=10)
Figure 2B:
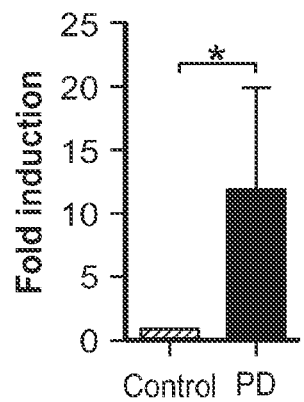
Figure 2C:
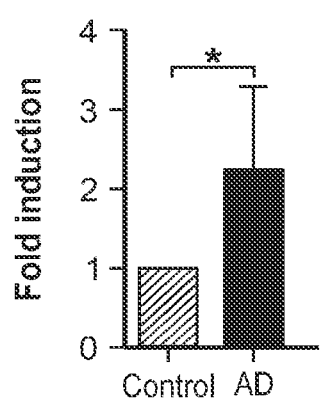

NLY001, a long-acting GLP-1r agonist, was identified to have targeted activated microglia transformed from resting microglia and simultaneously inhibited multiple inflammatory and neurotoxic mediators in neurodegenerative diseases. When primary microglia were activated by abnormally aggregated proteins, e.g. α-synuclein preformed fibrils (PFFs), activated microglia upregulated the mRNA levels of GLP-1r (FIG. 2A, FIG. 2B, and FIG. 2C). Brain tissues from patients with PD and AD exhibit upregulated GLP-1r compared to healthy brain tissues (FIG. 2A, FIG. 2B, and FIG. 2C). Importantly, when microglia are treated with α-synuclein PFFs (1 µg/ml) and NLY001 (1 µM) for 6 hr, NLY001 blocked microglial activation and significantly reduced the release of multiple inflammatory mediators including TNF-α, IL-1α, IL-1β and IL-6. In vivo, it was discovered that subcutaneously administered NLY001 simultaneously inhibits the levels of TNF-α, IL-1α, IL-1β, IL-6 and C1q (Table 1). This result indicates that a long-acting GLP-1r agonist is able to selectively target activated microglia through upregulated GLP-1r and simultaneously shut down the release of multiple inflammatory and toxic mediators that can induce neuronal damage in neurodegenerative diseases.

to see if it protects primary neurons against α-synuclein PFFs-activated microglia-mediated neuronal cell death. To address this, microglial cells were activated by α-synuclein PFFs (1 µg/ml) with or without NLY001 (1 µM) for 6 hr and then the culture media was washed out. Thereafter, primary neurons were co-cultured with activated microglia for 72 hr as described in FIG. 3. Neuronal toxicity was assessed by PI staining.

Results

As summarized in Table 2, neurons co-cultured with α-synuclein PFF-activated microglia showed increased cell death. In contrast, when neurons were co-cultured with microglial cells treated with PFFs and NLY001 demonstrated significantly reduced neuronal cell death. This results imply that NLY001 can protect neuronal cells from transformed microglial cells or astrocytes activated by abnormally aggregated proteins during the progression of neurodegenerative diseases.

TABLE 2

Neuronal cell death assay on primary microglia-primary cortical neurons co-culture.

| | Resting microglia + neurons | | PFF-activated microglia + neurons | |
| --- | --- | --- | --- | --- |
| | PBS | NLY001 (1 µM) | PBS | NLY001 (1 µM) |
| Cell death (%) | 8.7 ± 0.8 | 8.6 ± 1.6 | 46.1 ± 9.6*** | 13.8 ± 4.8### |

±S.E.M, n = 4 per groups.
Two-way ANOVA was used for statistical analysis and followed by post-hoc Bonferroni test for multiple group comparison.
***$P < 0.001$ vs. control group (PBS),
$P < 0.001$ vs. PFF + PBS group.

TABLE 1 mRNA levels (relative fold) of TNF-α, IL-1α, IL-1β and IL-6 in normal and α-synuclein PFFs activated mouse primary microglia treated with or without NLY001.

| | PBS | | a-synuclein PFF | |
| --- | --- | --- | --- | --- |
| mRNA | PBS | NLY001 (1 µM) | PBS | NLY001 (1 µM) |
| TNF-α | 1 ± 0.07 | 1.9 ± 0.27 | 113.2 ± 18.9*** | 11.3 ± 3.15### |
| IL-6 | 1 ± 0.02 | 1.6 ± 0.04 | 70.9 ± 0.75*** | 12.3 ± 2.38### |
| IL-1β | 1 ± 0.02 | 1.6 ± 0.02 | 506.5 ± 13.58*** | 57 ± 1.58### |
| IL-1α | 1 ± 0.02 | 1.5 ± 0.02 | 276.8 ± 4*** | 142.2 ± 4.1### |

±S.E.M, n = 3 per groups.
Two-way ANOVA was used for statistical analysis and followed by post-hoc Bonferroni test for multiple group comparison.
***$P < 0.001$ vs. control group (PBS),
$P < 0.001$ vs. PFF + PBS group.

Example 2: NLY001 Protects Neurons Against Activated Microglia-Mediated Neuronal Cell Death Materials and Methods To determine the effects of NLY001 on α-synuclein PFFs-induced microglial neurotoxicity, NLY001 was tested Example 3: A Long-Acting GLP-1r Agonist NLY001 Constitutively Activates GLP-1r Through Delayed GLP-1r Internalization Compared to Short-Acting GLP-1r Agonists Efficacy of short-acting GLP-1r agonists in clinically relevant, transgenic mouse models of neurodegenerative disease is not clear. For example, liraglutide (once daily injection) showed no effect on β-amyloid plaque load in 2×Tg AD models after a long-term treatment (Hansen H H et al. PLoS One. 2016. 11(7):e0158205). In PD, none of GLP-1r agonists (short-acting or long-acting) demonstrated the efficacy in clinically relevant Tg or mutant PD models. Overall, short-acting GLP-1r agonists proven efficacies in acute, toxin-based PD and AD models but not in chronic, transgenic models. Short-acting GLP-1r agonist may show reduced or no efficacy in chronic PD or AD models. Historically, the compounds proven efficacies only in toxin-based neurodegenerative models are mostly failed in clinical trials. In contrast, as described in the examples, NLY001 clearly demonstrated strong anti-PD and anti-AD efficacies in multiple and complementary chronic PD and AD models.

Unlike short-acting GLP-1r agonists, NLY001 is a long-acting GLP-1r agonist and unexpectedly penetrates BBB and show high accumulation in brain of neurodegenerative disease. It was hypothesized that short-acting GLP-1r agonists are not effective in chronic Tg models with neurodegenerative disease due to its lack of ability to continuously activate GLP-1r in the brain. Besides an extended plasma half-life of NLY001 that can continuously deliver active GLP-1 ligand to brain, it was identified that, at molecule level, NLY001 significantly delays GLP-1r internalization, therefore able to amplify GLP-1 singling, compared to that of short-acting GLP-1r agonists (Table 3). Therefore, combined with a long plasma half-life and the ability to penetrate BBB, NLY001 can continuously activate GLP-1r and induce GLP-1 signaling in target cells in brain without "off time" compare to short-acting GLP-1r agonists.

The GLP-1r internalization properties of short-acting and long-acting GLP-1r was investigated by using the PathHunter eXpress GLP1RA activated GRPC Internalization Assay kit (DisoverRX, CA). Briefly, the kit detects the interaction of arresting with the activated receptor using enzyme fragment complementation as described in the manufacture's manual. PathHunter eXpress activated GPCR internalization cells were plated in in a 96-well plate ($10^5$ cells per well) and stimulated with two short-acting GLP-1r agonists (exenatide and liraglutide) and a long-acting GLP-1r agonist, NLY001, at the concentrations of $10^{-12}$ to $10^{-6}$ M. Following stimulation, signal was detected according to the recommended protocols by the manufacture. As summarized in Table 3, NLY001 demonstrated 10 to 20-fold delay in GLP-1r internalization in terms of EC50 for agonist stimulation (nM) compare to short-acting GLP-1r agonists, exenatide and liraglutide.

TABLE 3

Internalization of human GLP-1r by short-acting and long-acting GLP-1r agonists.

| GLP-1r agonist | Short-acting GLP-1r agonist | | Long-acting GLP-1 agonist |
|---|---|---|---|
| | exenatide | liraglutide | NLY001 |
| EC50 for agonist stimulation (nM) | 6.5 ± 2.8 | 3.9 ± 2.9 | 60 ± 2.6[###] |

±S.E.M, n = 4 per groups.
Two-way ANOVA was used for statistical analysis and followed by post-hoc Bonferroni test for multiple group comparison.
[###]$P < 0.001$ vs short-acting GLP-1r agonists.

Example 4: NLY001 Reduces α-Synuclein Associated Gliosis (Microglia and Astrocytes Activation), Inhibits α-Synuclein Aggregation and Ameliorates LB/LN Pathology and Alleviates the Motor Deficit in α-Synuclein PFFs-Induced PD Mice Materials and Methods Animals All experimental procedures were followed according to the guidelines of Laboratory Animal Manual of the National Institute of Health Guide to the Care and Use of Animals, which were approved by the Johns Hopkins Medical Institute Animal Care and Use Committee. α-synuclein PFFs-induced PD mice were prepared (Luk, K. C., et al., Science, 2012. 338(6109): p. 949-53). For stereotaxic injection of α-synuclein PFF, 12 week-old male mice were anesthetized with xylazene and ketamine. An injection cannula (26.5 gauge) was applied stereotaxically into the striatum (anteroposterior, 3.0 mm from bregma; mediolateral, 0.2 mm; dorsoventral, 2.6 mm) unilaterally (applied into the right hemisphere). The infusion was performed at a rate of 0.2 μl per min, and 2 μl of α-synuclein PFF (5 ug/ml in PBS) or same volume PBS were injected into mouse. The head skin was closed by suturing and wound healing and recovery were monitored following surgery. For stereological analysis, animals were perfused and fixed intracardially with ice-cold PBS followed by 4% paraformaldehyde 6 month after striatal α-synuclein PFF injection. The brain was removed and processed for immunohistochemistry or immunofluorescence. Behavioral test was performed 6 months after the unilateral striatal α-synuclein PFF injection. Treatment of NLY001 (3 mg/kg) was accomplished after 1 month unilateral striatal α-synuclein PFF injection, 2 times per week, as described in FIG. 4A.

Beneficial Neuroprotective Effects of NLY001 Against α-Synuclein PFFs-Induced Behavioral Deficits The four different behavioral tests were conducted in vehicle (PBS) or NLY001 treated mice at 6 months after post α-synuclein PFFs injection.

Pole test: Animals were acclimatized in the behavioral procedure room for 30 min. The pole is made up 2.5 ft metal rod with 9 mm diameter and wrapped with bandage gauze. Briefly, the mice were placed on the top of the pole (3 inch from the top of the pole) facing the head-up. Total time taken to reach the base of the pole was recorded. Before the actual test the mice were trained for two consecutive days and each training session consists of three test trials. On the day of the test mice were evaluated in three sessions and total times were recorded. The maximum cutoff of time to stop the test and recording was 30 sec. Results were expressed in total time (in sec). α-synuclein PFFs injection led to a significant increase in the time to reach the base of the pole whereas treatment of NLY001 reduced the α-synuclein PFFs-induced behavioral deficit, similar to that of healthy mice (Table 4).

Rotarod test: For the rotarod test, mice were placed on an accelerating rotarod cylinder, and the time the animals remained on the rotarod was measured. The speed was slowly increased from 4 to 40 rpm within 5 minutes. A trial ended if the animal fell off the rungs or gripped the device and spun around for 2 consecutive revolutions without attempting to walk on the rungs. The animals were trained 3 days before test. Motor test data are presented as percentage of mean duration (3 trials) on the rotarod compared with the control. Treatment of NLY001 significantly improved the rotarod performance compared to that of PBS-treated PFFs-induced PD models (Table 4).

Cylinder test: Spontaneous movement was measured by placing animals in a small transparent cylinder (height, 15.5 cm; diameter, 12.7 cm). Spontaneous activity was recording for 5 min. The number of forepaw touch, rears and glooming were measured. Recording files were viewed and rated in slow motion by an experimenter blind to the mouse type and NLY001 treatment. A-synuclein PFFs-induced PD mice show deficits in forelimb use in the cylinder task while NLY001 treated PD mice alleviate the motor deficit with balanced use of both forepaws (Table 4).

Amphetamine induced stereotypic rotation: 5 mg/kg amphetamine (Sigma-Aldrich) was intraperitoneally administered into mice. Mice were placed into a white paper cylinder of 20 cm diameter and monitored for 30 minutes. The behavior of mice was filmed at three one-minute intervals between 20 and 30 minutes following amphetamine administration. Full body ipsilateral rotations (clockwise) during one minute session were counted for each mouse from the video recordings. α-synuclein injection increased the amphetamine induced rotational behavior by 7-fold indicating the loss of dopamine neurons. In contrast, NLY001 prevents the amphetamine induced rotation indicating that the dopamine neurons are functional (Table 4).

Next, the capability of NLY001 to ameliorate the spread of LB/Lewy neurites (LN)-like pathology induced by α-synuclein PFFs inoculation was investigated. After treatment as described above, deposits of hyperphosphorylated α-synuclein, a marker of human LB/LN, were visualized at the injection site (STR) and substantia nigra (SN) using the p-Syn$^{Ser129}$ antibody. p-Syn$^{Ser129}$ positive neurons showed a significant increase in LB/LN-like pathology in striatum and

TABLE 4

Behavioral test in healthy and α-synuclein PFFs-induced PD models (PFF).

| Test | Healthy PBS (SC) | Healthy NLY001 (SC) | PFF PBS (SC) | PFF NLY001 (SC) |
|---|---|---|---|---|
| Rotarod (latency to fall, sec) | 143.60 ± 8.28 | 156.66 ± 9.39 | 67.75 ± 6.48*** | 115.05 ± 7.34## |
| Pole test (Climb down time, sec) | 11.87 ± 1.25 | 9.91 ± 0.82 | 22.69 ± 1.17*** | 13.7 ± 1.07## |
| Cylinder test (Forepaw touch in 5 min) | 21.83 ± 1.35 | 21.54 ± 2.10 | 14.50 ± 2.08*** | 22.54 ± 2.05## |
| Amphetamine test (turn/min) | 1.57 ± 0.21 | 1.42 ± 0.23 | 7.13 ± 0.27*** | 2.29 ± 0.55### |

±S.E.M, n = 10 mice per groups.
Two-way ANOVA was used for statistical analysis and followed by post-hoc Bonferroni test for multiple group comparison.
***$P < 0.001$ vs. control group (PBS),
$P < 0.01$,
$P < 0.001$ vs. PFF injected group.

NLY001 Rescues Dopaminergic (DA) Neurons and Ameliorates LB Pathology in α-Synuclein PFFs-Induced PD Mice.

Accumulation of pathologic α-synuclein is linked to degeneration of DA neurons. As described herein, the capability of systemically administered NLY001 to protect against DA neuron loss induced by α-synuclein PFFs inoculation was examined. Mice were sacrificed and the loss of DA neurons was measured by counting the number of tyrosine hydroxylase (TH)-positive and Nissl-positive neurons in the SNpc using unbiased stereology. In addition, relative TH-positive fiber density in the striatum (STR) was analyzed by optical density measurement. Immunostaining of SNpc and STR sections and quantification of TH-positive stained DA neurons and fiber density show a significant loss of dopaminergic neurons in mice injected with PFFs compared to the PBS-treated controls. In contrast, administration of NLY001 significantly protects against PFFs-induced TH-neuronal loss (Table 5).

Figure 5:
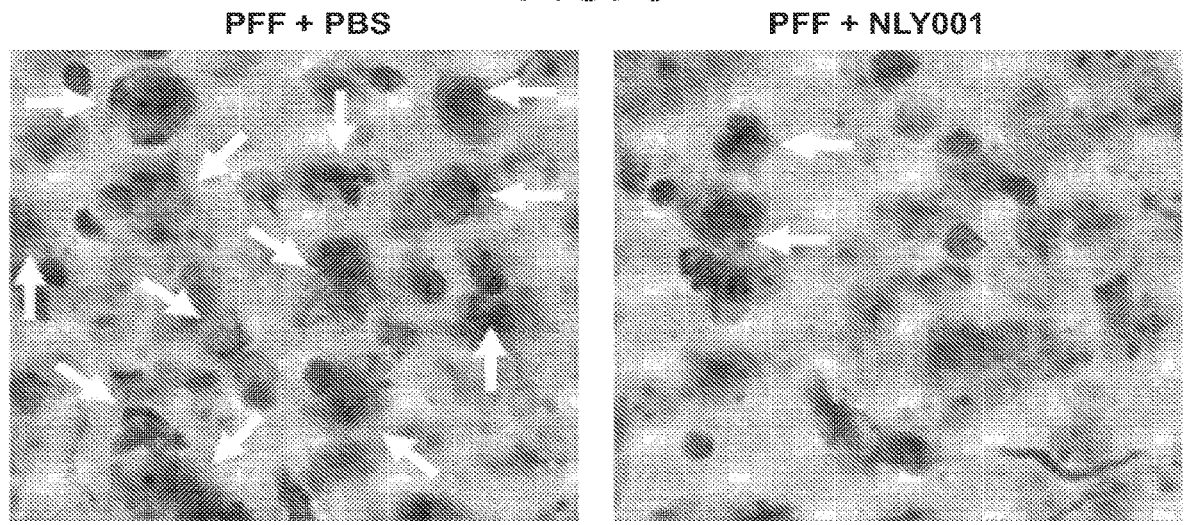
FIG. 5 is a series of photomicrographs showing NLY001 treatment in α-synuclein PFFs-induced PD mice significantly inhibits α-synuclein accumulation in the brain.

SN of mice injected with PFFs compared to PBS-treated controls. As shown in FIG. 5, NLY001 reduces the LB/LN pathology in the PD brain.

NLY001 Inhibits Gliosis in PD Brain by Reducing α-Synuclein Associated Microglia and Astrocytes Activation.

Microglia and astrocyte from the SNpc region were stained with anti-Iba-1 (1:1000, Wako) or anti-GFAP (1:2000, Dako) antibodies followed by incubation with biotin-conjugated anti-rabbit antibody and ABC reagents. And then sections were developed using SigmaFast DAB Peroxidase Substrate (Sigma-Aldrich, St. Louis, MO, USA). The number of microglia and densities of astrocyte in the SNpc region were measured with ImageJ software. In PD models, the cell populations of Iba-1-positive (activated microglia) and GFAP-positive (reactive astrocytes) are highly increased. NLY001 treatment significantly blocked microglia activation and decreased the formation of reactive astrocyte in PFFs-induced PD models (Table 6).

TABLE 5

NNY001 rescues DA neurons in a-synuclein PFFs-induced PD mice.

| Test | Healthy PBS (SC) | Healthy NLY001 (SC) | PFF (BI) PBS (SC) | PFF (BI) NLY001 (SC) |
|---|---|---|---|---|
| TH neuron in SNpc (×10$^4$) | 5.62 ± 0.51 | 5.77 ± 0.62 | 2.90 ± 0.37*** | 4.54 ± 0.27## |
| Nissle positive cells (×10$^4$) | 7.22 ± 0.56 | 7.41 ± 0.20 | 4.31 ± 0.26*** | 6.53 ± 0.44## |
| Relative fiber density in STR | 1.00 ± 0.07 | 0.972 ± 0.02 | 0.60 ± 0.06*** | 0.87 ± 0.04## |

±S.E.M, n = 10 mice per groups.
Two-way ANOVA was used for statistical analysis and followed by post-hoc Bonferroni test for multiple group comparison.
***$P < 0.001$ vs. control group (PBS),
$P < 0.01$ vs. PFF injected group.

TABLE 6

NLY001 blocks α-synuclein associated microglia and astrocyte activation in α-synuclein PFFs-induced PD mice.

| Test | Healthy PBS (SC) | Healthy NLY001 (SC) | PFF (BI) PBS (SC) | PFF (BI) NLY001 (SC) |
|---|---|---|---|---|
| Relative GFAP intensity | 1.00 ± 0.06 | 0.94 ± 0.04 | 1.92 ± 0.13*** | 1.31 ± 0.06### |
| Relative Iba-1 intensity | 1.00 ± 0.11 | 0.98 ± 0.09 | 2.66 ± 0.31*** | 1.55 ± 0.14### |
| Microglia density (cells/mm$^2$) | 26.50 ± 4.00 | 24.21 ± 4.55 | 138.22 ± 11.21*** | 55.12 ± 6.14### |

±S.E.M, n = 10 mice per groups.
Two-way ANOVA was used for statistical analysis and followed by post-hoc Bonferroni test for multiple group comparison.
***P < 0.001 vs. control group (PBS),
P < 0.001 vs. PFF injected group.

Example 5: NLY001 Reduces α-Synuclein Associated Gliosis (Microglia and Astrocytes Activation), Inhibits α-Synuclein Aggregation and Ameliorates LB/LN Pathology and Increases Lifespan in A53T Tg PD Mice Animals A53T α-synuclein transgenic mice (A53T) were obtained from Jackson Lab (B6; Prnp-SNCA*A53T, PMID: 12084935). The mice were mated with C57BL/6 mice (Jackson Lab), and were generated for the present study. NLY001 and PBS were subcutaneously treated (3 mg/kg, twice a week) in wild-type (WT) control mice and A53T PD mice after 6 month age until 10 month ages and death date, as described in FIG. 4B.

NLY001 Accumulates Significantly Higher in the PD Brain Compared to that of WT Mouse Brain.

Mice were sacrificed at 10 month ages and the concentration of NLY001 in brain (cerebellum and hemisphere) was measured by an immunoassay as described above. NLY001 was extracted from the brain tissues using C-18 SEP-Column (Phoenix Pharmaceuticals, Inc.) and analyzed by Exendin-4 EIA kit (Phoenix Pharmaceuticals Inc). Surprisingly, subcutaneously administered NLY001 penetrated BBB and accumulated significantly higher (10 to 30-fold) in the PD brain (A53T) compared to that of healthy WT mouse brain (Table 7).

TABLE 7

The brain accumulation of NLY001.

| Brain | WT PBS (SC) | WT NLY001 (SC) | A53T NLY001 (SC) |
|---|---|---|---|
| Cerebellum (pg per mg brain tissue) | 0.00 ± 0.00 | 28.48 ± 1.41 | 961.29 ± 202.73*** |
| Hemisphere (pg per mg brain tissue) | 3.00 ± 0.73 | 40.48 ± 2.6 | 445.55 ± 22.95*** |

±S.E.M, n = 6-8 mice per groups.
Two-way ANOVA was used for statistical analysis and followed by post-hoc Bonferroni test for multiple group comparison.
***P < 0.001 vs. control WT + NLY001 group.

NLY001 Treatment Increases Body Weight in PD Models.

Mouse models of advanced PD generally show decreased body weight. In clinic, weight loss in PD is a critical problem. Courses of PD that are complicated by weight loss result in poorer overall treatment outcome and lower quality of life. Approved GLP-1r agonists for diabetes/obesity patients are known to efficiently reduce body weight during a chronic treatment. Liraglutide especially is shown to be effective for long-term weight loss in type 2 diabetes and a high dose of liraglutide is recently approved as an anti-obesity drug (Sexenda). Unlike other GLP-1r agonists, NLY001 does not reduce body weight in neurodegenerative disease models and increases body weight while ameliorating the disease progression (Table 8).

TABLE 8

Body weight of WT and A53T PD mice models at 12-month ages treated with PBS or NLY001.

| Mice | WT PBS (SC) | WT NLY001 (SC) | A53T PBS (SC) | A53T NLY001 (SC) |
|---|---|---|---|---|
| Body weight (g) | 37.94 ± 0.56 | 38.76 ± 1.96 | 27.01 ± 0.28*** | 33.60 ± 0.50### |

±S.E.M, n = 20 mice per groups.
***P < 0.001 vs. control WT groups,
P < 0.001 vs. A53T + PBS group.

NLY001 Increases Lifespan of A53T α-Synuclein Tg Mice.

Figure 6:
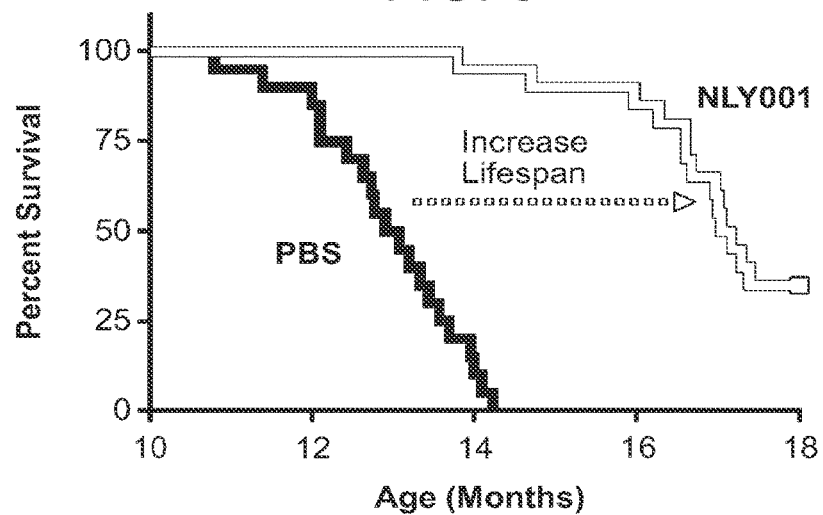
FIG. 6 shows Kaplan-Meier survival curve analysis for hA53T α-synuclein transgenic (Tg) PD mice with PBS or NLY001. Mice were treated with vehicle (PBS) or NLY001 at 6-month of age.

A53T α-synuclein Tg mice display shortened lifespan owing to degeneration of brainstem and spinal cord neurons leading to limb paralysis, automic dysfunction and premature death (Lee M K et al. Proc Natl Acad Sci USA. 2002. 99(13):8969-8973). In most affected animals, the disease rapidly progressed to death, potentially because of the inability to feed and dehydration. In this study, A53T mice exhibited premature lethality ranging from 11 to 14 months of age. In contrast, NLY001 treatment significantly increased lifespan of A53T (FIG. 6 and Table 9).

TABLE 9

Median survival is calculated by GraphPad Prism 6.

| Mice | WT PBS (SC) | WT NLY001 (SC) | A53T PBS (SC) | A53T NLY001 (SC) |
|---|---|---|---|---|
| Median Survival (month) | no death | no death | 12.9 | 17.1[###] |

±S.E.M, n = 20 mice per groups.
[###]P < 0.001 vs. A53T + PBS group.

NLY001 Inhibits Gliosis in PD Brain and Reduce α-Synuclein Aggregation in A53T α-Synuclein Tg PD Mice.

Microglia and astrocyte activations were analyzed as described above. The number of microglia and densities of astrocyte in the brain were measured with ImageJ software. In A53T Tg PD models, the cell populations of Iba-1-positive (activated microglia) and GFAP-positive (reactive astrocytes) were highly increased. NLY001 treatment significantly blocked microglia activation and decreased the formation of reactive astrocyte in A53T Tg PD models (Table 10). Importantly, the relative protein expressions of α-synuclein$^{p-ser129}$, α-synuclein aggregation and β-actin were analyzed by immunoblots in the detergent insoluble fraction of brain stem from 10-month-old A53T Tg mice and age-matched littermate controls with PBS or NLY001. In addition, the formation of ubiquitin-positive inclusions in the brain stem of A53T Tg mice was analyzed by p-α-synuclein immunohistochemistry images. As seen in PFFs-induced PD mice, NLY001 significantly blocked α-synuclein aggregation in A53T Tg PD mice. The results are summarized in Table 11.

TABLE 11

NLY001 reduces the expressions of a-synuclein and ubiquitin in A53T α-synucelin Tg PD mice.

| Test | A53T PBS (SC) | A53T NLY001 (SC) |
|---|---|---|
| Relative α-synuclein$^{p-ser129}$ | 1.00 ± 0.10 | 0.48 ± 0.06[###] |
| Relative α-synuclein aggregation | 1.00 ± 0.04 | 0.43 ± 0.05[###] |
| Relative Ubiquitin intensity | 1.00 ± 0.08 | 0.52 ± 0.06[###] |

±S.E.M, n = 3 mice per groups.
Two-way ANOVA was used for statistical analysis and followed by post-hoc Bonferroni test for multiple group comparison.
[###]P < 0.001 vs. A53T + PBS group.

Figure 7:
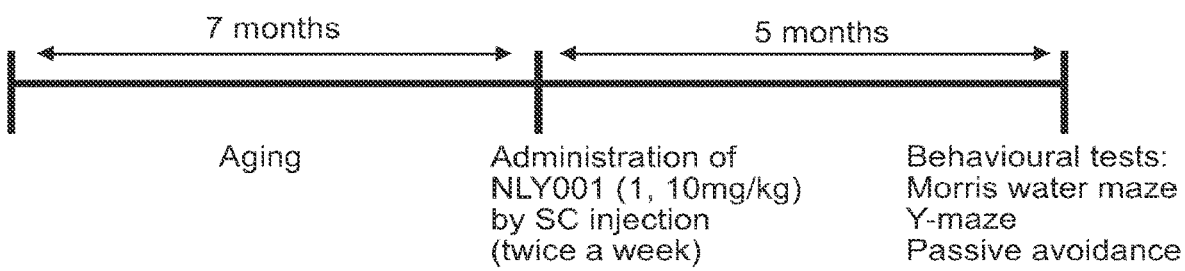
FIG. 7 shows a timeline that depicts the experimental strategy in AD mouse models.

Example 6: NL YOOI Ameliorates Alzheimer's Disease-Like Pathology and Memory Impairment in 3×Tg AD Mice Materials and Methods Animals: 3×Tg AD mice were obtained from Jackson Lab. These widely used mice contain three mutations, AAP Swedish, MAPT 3P01L and PSEN1 M126V, associated with familial Alzheimer's disease. 3×Tg mice display both plaque and tang pathology. B-amyloid deposition is progressive and appear intracellularly as early as three of four months of age and extracellular deposits appear by six months in the frontal cortex and become more extensive by twelve months. In this study, 6-month old male 3×Tg AD mice were used. NLY001 and PBS were subcutaneously treated (1 mg/kg and 10 mg/kg, twice a week) in wild-type (WT) control mice and 3×Tg AD mice after 7-month ages for 5 months, as described in FIG. 7.

NLY001 Improves Memory in 3×Tg AD Mice. Two Different Behavioral Tests (Webster S J et al., Front Genet. 2014. 5:88) were Conducted in Vehicle (PBS) or NLY001 Treated Mice.

Morris water maze test (MWM): The Morris water maze is a white circular pool (100 cm in diameter and 35 cm in height) with a featureless inner surface. The circular pool was filled with water and a nontoxic water-soluble white dye. The pool was divided into four quadrants of equal area. A platform (8 cm in diameter and 10 cm in height) was centered in one of the quadrants of the pool and submerged 1 cm below the water surface so that it was invisible at water level. The pool was located in a test room that contained various prominent visual cues. The location of each swimming mouse, from the start position to the platform, was monitored by a video tracking system (ANY-maxe system,

TABLE 10

NLY001 blocks α-synuclein associated microglia and astrocyte activation in A53T α-synuclein Tg PD mice.

| Test | WT PBS (SC) | WT NLY001 (SC) | A53T PBS (SC) | A53T NLY001 (SC) |
|---|---|---|---|---|
| Relative GFAP intensity | 1.00 ± 0.04 | 0.98 ± 0.08 | 1.95 ± 0.05[***] | 1.24 ± 0.03[##] |
| Relative Iba-1 intensity | 1.00 ± 0.11 | 0.98 ± 0.09 | 2.66 ± 0.31[***] | 1.55 ± 0.14[##] |
| Microglia density (cells/mm$^2$) | 29.10 ± 3.00 | 27.33 ± 2.89 | 141.33 ± 8.49[***] | 50.66 ± 5.06[###] |

±S.E.M, n = 7 mice per groups.
Two-way ANOVA was used for statistical analysis and followed by post-hoc Bonferroni test for multiple group comparison.
[***]P < 0.001 vs. control group (PBS),
[##]P < 0.01,
[###]P < 0.001 vs. A53T + PBS group.

Wood Dale, IL, USA). The day before the experiment was dedicated to swim training for 60s in the absence of the platform. The mice were then given three trial sessions each day for five consecutive days, with an inter-trial interval of 15 min, and the escape latencies were recorded. This parameter was averaged for each session of trials and for each mouse. Once the mouse located the platform, it was permitted to remain on it for 10s. If the mouse did not locate the platform within 60s, it was placed on the platform for 10s and then removed from the pool by the experimenter. On day 6, the probe test involved removing the platform from the pool. That test was performed with the cut-off time of 60s. The point of entry of the mouse into the pool and the location of the platform for escape remained unchanged between trial 1 and 2 but was changed each day thereafter.

Figure 3:
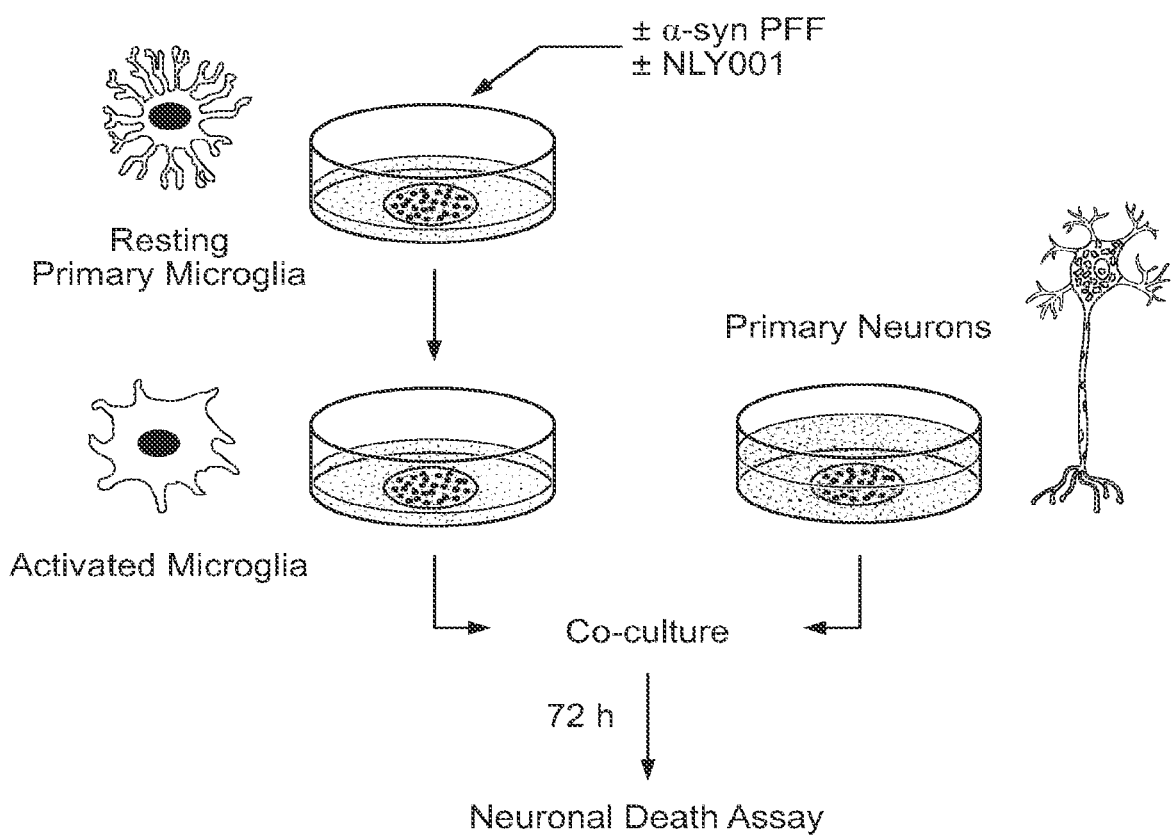
FIG. 3 is a schematic showing the activated microglia-neuron co-culture experiments. Primary microglia were activated by α-synuclein with or without NLY001 and microglia were co-cultured with primary neurons for 72 hours followed by neuronal death assays.
Figure 8:
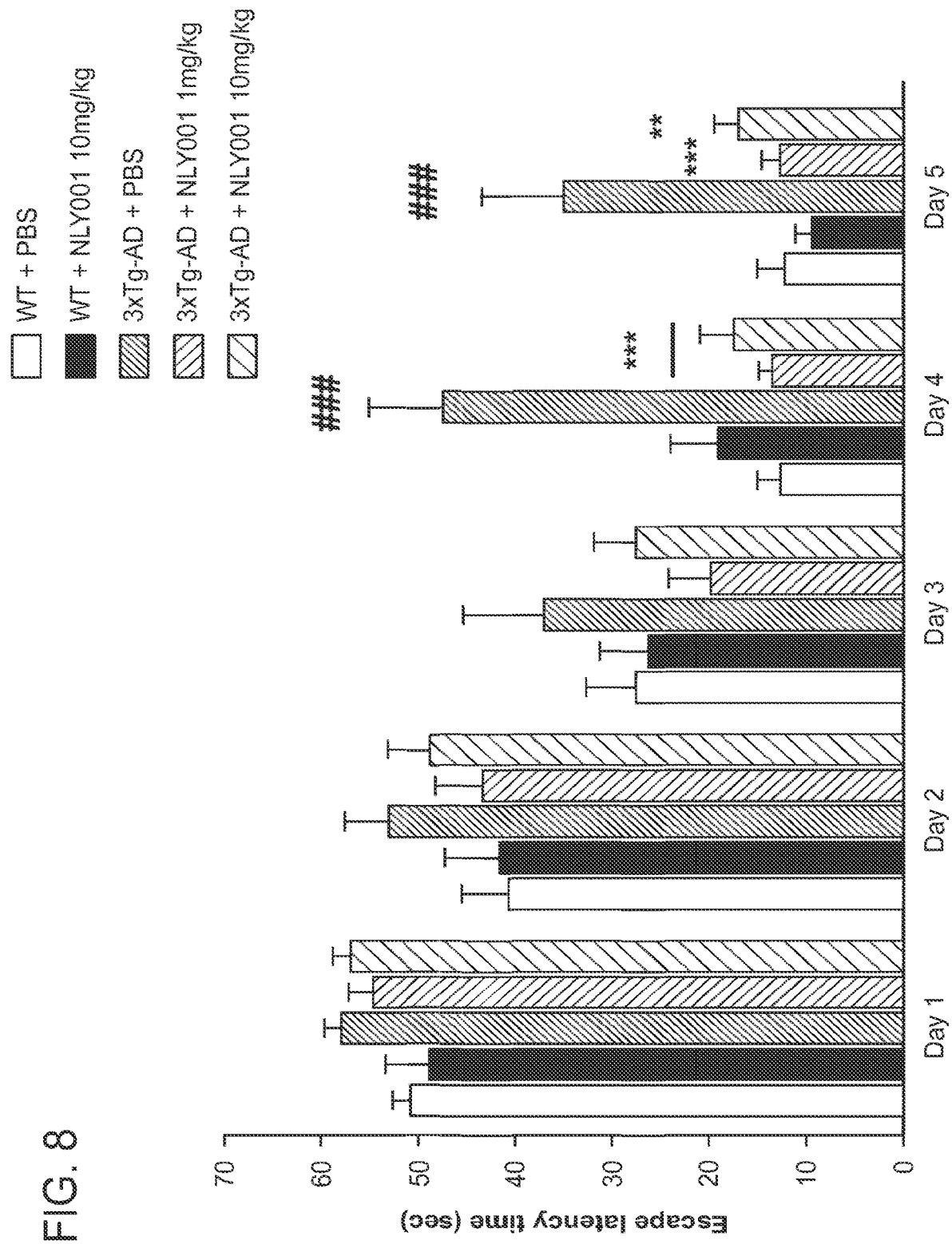
FIG. 8 is a graph showing the results of a Morris water maze (MWM) test on NLY001 treated 3×Tg-AD mice. ±S.E.M, n=7 mice per groups. ####P<0.001 vs. WT+PBS group. P<0.01, P<0.001 vs. 3×Tg AD+PBS.
Figure 9:
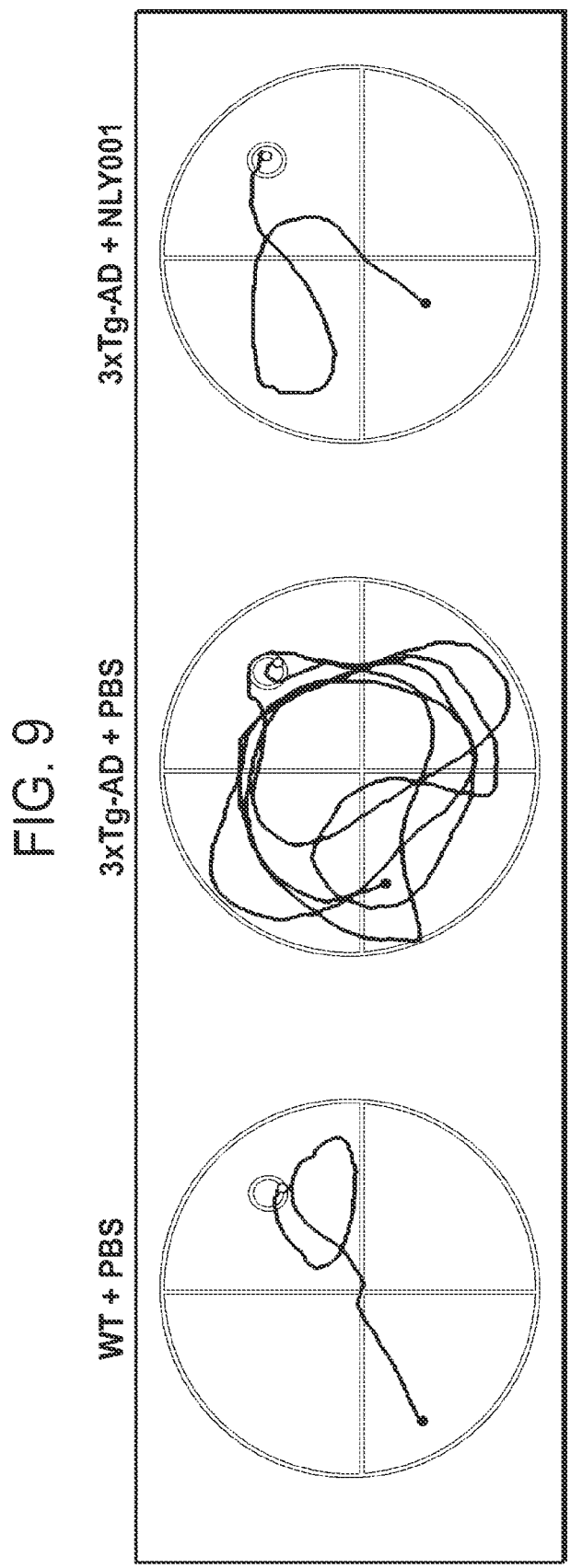
FIG. 9 is a series of images showing representative video tracking of wild-type (WT) and 3×Tg-AD mice treated with vehicle (PBS) or NLY001.

As described in FIG. 8 and FIG. 9, 3×Tg AD mice treated with PBS showed defects in learning compared with the WT mice. On day 4 and day 5, PBS treated 3×Tg mice spent more time than WT littermates to locate the hidden platform. In contrast, NLY001 treated 3×Tg AD mice showed significantly improved performance compared to that of PBS treated 3×Tg mice, indicating that the NLY001 treatment alleviated the impairment of spatial learning in 3×Tg mice. To assess the memory strength of spatial learning, the probe trials were examined on day 5. NLY001 treated 3×Tg mice spent significantly more time searching for the platform in the target quadrant compared to PBS treated 3×Tg AD mice (Table 12). NLY001 treatment did no influence the swimming velocity and distance.

TABLE 12

Probe test and swimming test on NLY001 treated 3xTg AD mice.

| | WT | | 3xTg-AD | | |
| --- | --- | --- | --- | --- | --- |
| Probe test | PBS | NLY001 10 mg/kg | PBS | NLY001 1 mg/kg | NLY001 10 mg/kg |
| Swimming time in the target quadrant (sec) | 26.26 ± 5.49 | 27.02 ± 4.19 | 17.52 ± 9.63* | 24.49 ± 6.17# | 32.66 ± 7.16### |
| Swimming speed (m/s) | 0.21 ± 0.02 | 0.19 ± 0.02 | 0.20 ± 0.03 | 0.20 ± 0.02 | 0.20 ± 0.02 |

±S.E.M, n = 7 mice per groups.
*$P < 0.05$ vs. WT + PBS,
$P < 0.05$,
$P < 0.001$ vs. 3xTg AD + PBS group.

Passive avoidance test: The effects of NLY001 learning/memory were assessed by means of a step-through passive avoidance procedure, in which animals learn to avoid an electrical discharge by suppressing their natural preference for dark environments. Testing began with a training in which a mouse was placed in a lighted chamber; when the mouse crossed over to the dark chamber, it received a mild (0.25 mA/1 s) footshock. This initial latency to enter the dark (shock) compartment served as the baseline measure. During the probe trials, 24 hr after training, the mouse was again placed in the light compartment, and the latency to return to the dark compartment was measured as an index of passive fear avoidance. NLY001 treatment significantly improved learning in 3×Tg AD mice assessed by the passive avoidance test compared to that of PBS-treated 3×Tg AD mice (Table 13).

TABLE 13

Learning assessed by the passive avoidance test in WT and 3xTg AD mice treated with PBS or NLY001.

| | WT | | 3xTg-AD | | |
| --- | --- | --- | --- | --- | --- |
| Passive avoidance | PBS | NLY001 10 mg/kg | PBS | NLY001 1 mg/kg | NLY001 10 mg/kg |
| Time to enter dark (sec) | 213.3 ± 93.3 | 242.4 ± 96.7 | 148.0 ± 125.2* | 242.1 ± 91.5# | 228.9 ± 121.7# |

The Error bars represent the mean ± S.E.M, n = 7 mice per groups.
*$P < 0.05$ vs. WT + PBS,
$P < 0.05$ vs. 3xTg AD + PBS group.

NLY001 Accumulates Significantly Higher in the AD Brain Compared to that of WT Mouse Brain.

As described in PD models, mice were sacrificed after the study and the concentration of NLY001 in the whole brain was measured by an immunoassay as described above. NLY001 was extracted from the brain tissues using C-18 SEP-Column and analyzed by Exendin-4 EIA kit. As proven in PD models, subcutaneously administered NLY001 penetrated BBB and accumulated two to five-fold higher in the 3×Tg AD brain compared to that of healthy WT mouse brain.

NLY001 Inhibits Gliosis in AD Brain by Reducing Microglia and Astrocytes Activation.

Microglia and astrocyte from the fixed brain tissues were stained with anti-Iba-1 or anti-GFAP antibodies followed by incubation with biotin-conjugated anti-rabbit antibody and ABC reagents as described above. In AD models, the cell populations of Iba-1-positive (activated microglia) and GFAP-positive (reactive astrocytes) are highly increased. NLY001 treatment significantly blocked microglia activation and decreased the formation of reactive astrocyte in 3×Tg AD models. In addition, it was also validated that GLP-1r is highly expressed on the Iba-1-positive cells (activated microglia) but not on the MAP2-positive cells (neuron). This results support the in vitro findings, a long-acting GLP-1r agonist block gliosis and shut down the release of inflammatory and neurotoxic molecules by binding to GLP-1r expressed on the resident innate immune cells including microglia in brain.

NLY001 Treatment Reduces the Expression of Inflammatory and Neurotoxic Molecules in the Brain of 3×Tg AD Mice.

To further confirm if anti-AD efficacy of NLY001 in 3×Tg mice is due to inhibition of the release of inflammatory and neurotoxic molecules secreted from activated microglia and reactive astrocytes, brain tissue homogenates were analyzed by real-time PCR for TNF-α, IL-1β, IFN-γ, IL-6, and C1q. It was found that the expression levels of inflammatory markers are significantly higher in 3×Tg mice compared to WT mice. Consistent with the study results in vitro cells, NLY001 treated 3×Tg mice demonstrated significantly reduced the expression of inflammatory and neurotic markers as summarized in Table 14.

EQUIVALENTS

Those skilled in the art will recognize, or be able to ascertain using no more than routine experimentation, many equivalents to the specific embodiments of the invention described herein. Such equivalents are intended to be encompassed by the following claims.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

TABLE 14

Effects of NLY001 in 3xTg AD mice.

| | WT | | 3xTg-AD | | |
| --- | --- | --- | --- | --- | --- |
| mRNA | PBS | NLY001 10 mg/kg | PBS | NLY001 1 mg/kg | NLY001 10 mg/kg |
| TNF-α | 1.0 ± 0.5 | 1.0 ± 0.4 | 3.7 ± 3.1** | 1.8 ± 0.5# | 2.0 ± 0.7# |
| IL-1β | 1.0 ± 0.4 | 0.9 ± 0.5 | 2.9 ± 1.4*** | 1.4 ± 0.5## | 1.6 ± 0.9## |
| IFN-γ | 1.0 ± 0.7 | 0.6 ± 0.3 | 5.3 ± 5.7** | 1.4 ± 0.5# | 1.6 ± 0.8## |
| IL-6 | 1.0 ± 0.4 | 0.8 ± 0.1 | 1.9 ± 0.4* | 1.4 ± 0.4 | 1.1 ± 0.3# |
| C1q | 1.0 ± 0.3 | 1.0 ± 0.1 | 1.6 ± 0.3* | 1.2 ± 0.3 | 1.1 ± 0.2# | mRNA levels of TNF-α, IL-1β, IFN-γ, IL-6, and C1q in the brain were analyzed by real-time PCR.
±S.E.M, n = 5 mice per groups.
*$P < 0.05$,
**$P < 0.01$,
***$P < 0.001$ vs. WT + PBS,
$P < 0.05$,
$P < 0.01$ vs. 3xTg AD + PBS group.

What is claimed is:

1. A method of treating a subject in need thereof, the method comprising
administering to a subject with a disease selected from the group consisting of Parkinson's disease, Alzheimer's disease, Huntington's disease, amyotrophic lateral sclerosis, spinocerebellar ataxia type 1, and multiple sclerosis a pharmaceutically effective amount of a composition comprising a GLP-1r agonist PEGylated with polyethylene glycol (PEG) or derivatives thereof, which penetrates the blood brain barrier.

2. The method of claim 1 comprising administering to a subject in need thereof the composition comprising an amount of a long-acting GLP-1r agonist effective to block activation of resident innate immune cells.

3. The method of claim 2, wherein abnormally aggregated proteins are inhibited from activating immune cells through upregulation of GLP-1r.

4. The method of claim 2, wherein the amount of a long-acting GLP-1r agonist is effective to inhibit the secretion of inflammatory and/or neurotoxic mediators secreted from the activated innate immune cells.

5. The method of claim 2, wherein the innate immune cells are microglia and/or astrocytes.

6. The method of claim 3, wherein the abnormally aggregated proteins are β-synuclein, β-amyloid or tau.

7. The method of claim 5, wherein the effective amount of a long-acting GLP-1r agonist reduces the cell populations of activated microglia and reactive astrocytes.

8. The method of claim 1, wherein the long-acting GLP-1r agonist comprises a PEGylated exenatide analog.

9. The method of claim 1, wherein the composition is administered via oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

10. The method of claim 9, wherein the composition is administered subcutaneously.

11. The method of claim 1, wherein the composition is administered in a form selected from the group consisting of liquids and suspensions.

12. The method of claim 1, wherein the composition is administered once a week.

13. The method of claim 1, wherein the composition is administered every two weeks.

14. The method of claim 1 wherein the composition is administered approximately once a month.

15. The method of claim 1, wherein the composition is administered once every two months.

16. The method of claim 1, wherein the GLP-1r agonist is administered between one and three times every 6 months.

17. The method of claim 1, wherein the GLP-1r agonist has a half-life in vivo of between 12 hours and 200 hours in non-human primates or humans.

18. The method of claim 1, wherein the GLP-1r agonist is administered to a human at a dose between 0.001 mg/kg and 10 mg/kg.

19. The method of claim 1, wherein the PEG or the derivative thereof has a molecular weight between about 20 kDa and about 250 kDa.

20. The method of claim 1, wherein the PEG or the derivative thereof has a molecular weight between about 30 kDa and about 250 kDa.

21. The method of claim 1, wherein the PEG or the derivative thereof has a molecular weight between about 30 kDa and about 100 kDa.

22. The method of claim 1, wherein the method reduces or prevents body weight loss in the subject.

23. The method of claim 1, wherein the GLP-1r agonist has a half-life in vivo of between 20 hours and 200 hours in non-human primates or humans.

24. The method of claim 1, wherein the GLP-1r agonist has a half-life in vivo of about 88 hours in non-human primates or humans.

25. The method of claim 1, wherein the GLP-1r agonist is administered to a human at a dose between 0.1 mg/kg and 100 mg/kg.

26. The method of claim 1 wherein the subject has Parkinson's disease.

27. The method of claim 1 wherein the subject has Alzheimer's disease.

28. The method of claim 1 wherein the subject has Huntington's disease.

29. The method of claim 1 wherein the subject has amyotrophic lateral sclerosis.

30. The method of claim 1 wherein the subject has spinocerebellar ataxia type 1.

31. The method of claim 1 wherein the subject has multiple sclerosis.

32. The method of claim 1 comprising measuring a change in the levels of a compound selected from the group consisting of TNF-$\alpha$, IL-1$\beta$, IL-1$\alpha$, INF-$\gamma$, IL-6, and C1q.

* * * * *